(12) United States Patent
Fukuhara et al.

(10) Patent No.: US 10,456,351 B2
(45) Date of Patent: *Oct. 29, 2019

(54) ORGANOPOLYSILOXANE

(71) Applicant: KAO CORPORATION, Tokyo (JP)

(72) Inventors: Kazuhisa Fukuhara, Sumida-ku (JP);
Takashi Kodate, Wakayama (JP);
Kayoko Kitada, Sumida-ku (JP);
Kenichi Ueyama, Sumida-ku (JP);
Masayoshi Ehara, Darmstadt (DE)

(73) Assignee: KAO CORPORATION, Tokyo (JP)

( * ) Notice: Subject to any disclaimer, the term of this patent is extended or adjusted under 35 U.S.C. 154(b) by 40 days.

This patent is subject to a terminal disclaimer.

(21) Appl. No.: 15/000,284

(22) Filed: Jan. 19, 2016

(65) Prior Publication Data
US 2016/0128928 A1 May 12, 2016

Related U.S. Application Data

(63) Continuation of application No. 12/669,045, filed as application No. PCT/JP2008/063474 on Jul. 18, 2008, now abandoned.

(30) Foreign Application Priority Data

| Jul. 20, 2007 | (JP) | 2007-190244 |
| Jul. 20, 2007 | (JP) | 2007-190245 |
| Dec. 7, 2007  | (JP) | 2007-316589 |

(51) Int. Cl.
*A61K 8/898* (2006.01)
*A61Q 5/06* (2006.01)
*C08G 77/452* (2006.01)
*C08G 81/00* (2006.01)
*C08G 77/26* (2006.01)

(52) U.S. Cl.
CPC .......... *A61K 8/898* (2013.01); *A61Q 5/06* (2013.01); *C08G 77/452* (2013.01); *C08G 81/00* (2013.01); *A61K 2800/54* (2013.01); *C08G 77/26* (2013.01)

(58) Field of Classification Search
CPC ...... A61K 2800/54; A61K 8/898; A61Q 5/06; C08G 77/26; C08G 77/452; C08G 81/00
See application file for complete search history.

(56) References Cited

U.S. PATENT DOCUMENTS

| 5,464,917 | A | * | 11/1995 | Kishita | C08G 77/24 528/14 |
| 5,472,689 | A | * | 12/1995 | Ito | A61Q 5/06 424/70.122 |
| 5,618,525 | A | * | 4/1997 | Bunning | A61K 8/898 424/70.122 |
| 5,747,016 | A | * | 5/1998 | Yui | A61K 8/898 424/401 |
| 5,904,919 | A | * | 5/1999 | Brautigam | A61K 8/46 424/70.122 |
| 5,981,679 | A | * | 11/1999 | Takei | C07F 7/0852 526/279 |
| 6,027,718 | A | * | 2/2000 | Takiguchi | A61K 8/898 424/401 |
| 6,440,429 | B1 |  | 8/2002 | Torizuka et al. | |
| 6,827,944 | B2 | * | 12/2004 | Hosokawa | A61K 9/7015 424/449 |
| 2003/0035826 | A1 | * | 2/2003 | Hosokawa | A61K 9/7015 424/449 |
| 2006/0045862 | A1 | * | 3/2006 | Tada | A61K 8/34 424/70.122 |

(Continued)

FOREIGN PATENT DOCUMENTS

| EP | 0 640 643 A2 | 3/1995 |
| EP | 0 640 643 A3 | 3/1995 |

(Continued)

OTHER PUBLICATIONS

Office Action dated Dec. 25, 2012, in Japanese Patent Application No. 2007-190245, filed Jul. 20, 2007 (with English translation).

*Primary Examiner* — Robert A Wax
*Assistant Examiner* — Olga V. Tcherkasskaya
(74) *Attorney, Agent, or Firm* — Oblon, McClelland, Maier & Neustadt, L.L.P.

(57) ABSTRACT

There is provided an organopolysiloxane which is excellent in extensibility as well as solubility and dispersibility in water and lower alcohols. There is provided an organopolysiloxane with a poly(N-acylalkyleneimine) segment having a repeating unit represented by the following general formula (1):

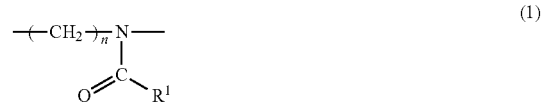

(1)

wherein $R^1$ represents a hydrogen atom or an alkyl group, an aralkyl group, or an aryl group each having 1 to 22 carbon atoms, and n is 2 or 3, wherein the segment is bound to each of at least two silicon atoms of an organopolysiloxane segment as a main chain via an alkylene group containing a hetero atom, and wherein the number-average molecular weight of the segment is 800 to 1600, the mass ratio of the organopolysiloxane segment as a main chain and the poly (N-acylalkyleneimine) segment is 65/35 to 82/18, and the weight-average molecular weight of the organopolysiloxane segment as a main chain is 10,000 to 100,000.

20 Claims, No Drawings

(56) References Cited

U.S. PATENT DOCUMENTS

| | | | |
|---|---|---|---|
| 2010/0203002 A1 | 8/2010 | Fukuhara et al. | |
| 2011/0067721 A1* | 3/2011 | Tate | A61K 8/046 132/203 |
| 2012/0216823 A1* | 8/2012 | Fukuhara | A61K 8/898 132/203 |
| 2013/0104923 A1* | 5/2013 | Sakai | A61K 8/8194 132/202 |
| 2013/0247931 A1* | 9/2013 | Fukuhara | A61Q 5/06 132/206 |

FOREIGN PATENT DOCUMENTS

| | | |
|---|---|---|
| EP | 0 761 202 | 3/1997 |
| JP | 2 276824 | 11/1990 |
| JP | 2-276824 | 11/1990 |
| JP | 3-287509 | 12/1991 |
| JP | 3 287509 | 12/1991 |
| JP | 4-85334 | 3/1992 |
| JP | 4 85334 | 3/1992 |
| JP | 6-298625 | 10/1994 |
| JP | 7 133352 | 5/1995 |
| JP | 9 202714 | 8/1997 |
| JP | 10 95705 | 4/1998 |
| JP | 10 306163 | 11/1998 |
| JP | 2002-53444 | 2/2002 |
| JP | 2006 69899 | 3/2006 |
| JP | 2009-24114 | 2/2009 |

* cited by examiner

ORGANOPOLYSILOXANE

CROSS REFERENCES TO RELATED APPLICATIONS

This application is a Continuation Application of U.S. patent application Ser. No. 12/669,045, filed on Jan. 14, 2010, which was a 371 of International Patent Application No. PCT/JP08/063474, filed on Jul. 18, 2008, and claims priority to Japanese Patent Application No. 2007-190244, filed on Jul. 20, 2007, Japanese Patent Application No. 2007-190245, filed on Jul. 20, 2007, and Japanese Patent Application No. 2007-316589, filed on Dec. 7, 2007.

FIELD OF THE INVENTION

The present invention relates to a novel organopolysiloxane and a hair cosmetic containing the same.

BACKGROUND OF THE INVENTION

Since organopolysiloxanes (hereinafter sometimes referred to as "silicones") have many features such as low surface tension, excellent lubricating property and mold releasing property, high thermal stability, generally very low glass transition points, and excellent gas permeability, silicones in various forms are very widely used as lubricants, heat medium, electric insulators, paint leveling agents, mold releasing agents, cosmetic additives, textile treating agents, shock buffering materials, sealing materials, molding materials, polishing agents, foam stabilizers, and defoaming agents.

The cosmetic field is no exception, and silicones are often used as feel improving agents or the like in cosmetic products such as skin care agents, foundations, shampoos, and conditioners. As an example of silicones that can be used in cosmetics, organopolysiloxanes that do not break or are not plastically deformed at extension rates in the range of 0 to 15% at a temperature of 20° C. and a relative humidity of 65% have been disclosed in JP-A-07-133352. Hair cosmetics containing these organopolysiloxanes have excellent hair setting ability and set holding performance, can impart a favorable feel such as flexibility and no stiffness to the hair after setting, and can be easily washed off by shampooing the hair. Thus, the organopolysiloxanes described in JP-A-07-133352 were superior to conventional set polymers.

In recent years, however, required performance and preference in hair cosmetics have been greatly changed, and conventional set polymers or silicones cannot adequately respond to them. Specifically, hair cosmetics are required to impart a flexible feel, have set characteristics that the hair style is not disintegrated after passing fingers through the hair, and, in addition, achieve a more natural finish.

Meanwhile, it is said that chemical treatment with hair color or the like and physical treatment such as blowing cause abrasion of cuticles on the hair surface and hollowing of the hair due to the leakage of lipids from the inside of the hair, resulting in overly dry hair, uneasy finger passing, poor hair manageability, and loss of luster.

To impart manageability to the hair and prevent overly dry hair, hair cosmetics mainly used at present include waxes, emulsified products such as hair creams containing oil solutions such as a higher alcohol, a surfactant, and the like, gels containing a membrane formation polymer (set polymer), and so forth. Such hair cosmetics attach oils and fats or polymers to the hair surface to solve problems such as poor manageability and overly dry hair only temporarily, but could not achieve essential improvement.

Several hair cosmetics for reforming the hair are known, and some of these use specific organic acids and organic solvents for reforming the hair by acting on the inside of the hair. However, while such hair cosmetics have excellent reforming effects to improve luster and manageability of the hair, they suffer from such problems that flexibility is hard to impart, the applied hair becomes greasy, and so forth. Therefore, common silicones are mixed as feel improving agents. However, although the feel to the touch is improved, a problem arises that hair reforming effects (improvement of manageability, etc.) by organic acids and organic solvents are impaired.

To solve such problems, a hair cosmetic has been proposed in which an organopolysiloxane having a specific structure is used in combination with a specific organic acid and a specific organic solvent (JP-A-2006-69899).

Furthermore, due to diversified and individualized hair styles in recent years, hair cosmetics are desired wherein a desired hair style can be easily set, the set hair style can be held for a long time, and a flexible feel and a more natural finish can be imparted. While the above-mentioned hair cosmetic of JP-A-2006-69899 can impart a favorable feel (softness, no greasiness, etc.) without impairing hair reforming effects (improvement of manageability, etc.), neither of styling properties, setting performance and set holding performance, is necessarily adequate, and these properties have room to improve.

JP-A-07-133352
JP-A-2006-69899

SUMMARY OF THE INVENTION

The present invention provides an organopolysiloxane with a poly(N-acylalkyleneimine) segment having a repeating unit represented by the following general formula (1) bound to each of at least two silicon atoms of an organopolysiloxane segment as a main chain via an alkylene group containing a hetero atom, wherein the number-average molecular weight of the poly(N-acylalkyleneimine) segment is 800 to 1600, the mass ratio (a/b) of the organopolysiloxane segment (a) as a main chain and the poly(N-acylalkyleneimine) segment (b) is 65/35 to 82/18, and the weight-average molecular weight of the organopolysiloxane segment as a main chain is 10,000 to 100,000.

(1)

wherein $R^1$ represents a hydrogen atom or an alkyl group, an aralkyl group, or an aryl group each having 1 to 22 carbon atoms, and n is 2 or 3.

Furthermore, the present invention provides a hair cosmetic containing the above-mentioned organopolysiloxane.

DETAILED DESCRIPTION OF THE INVENTION

The present invention provides an organopolysiloxane having excellent extensibility and excellent solubility and dispersibility in water and lower alcohols, and a hair cosmetic containing the same.

The inventors of the present invention found that, among organopolysiloxanes having a structure similar to that of the organopolysiloxanes described in the above-mentioned JP-A-07-133352, those in a specific scope have properties totally different from the organopolysiloxanes described in JP-A-07-133352, specifically, they cause plastic deformation and exhibit much superior extensibility.

Conventionally, polymers causing plastic deformation have an inadequate set holding performance and have been thought to be unsuitable as polymers for hair setting. Unexpectedly, however, it has been found that, when an organopolysiloxane that causes plastic deformation and has high extensibility is added to a hair cosmetic, a flexible feel can be imparted, the set hair is minimally disintegrated even when fingers are passed through the hair or external factors such as wind and vibration are applied, a natural finish is achieved, and a favorable wash property is exhibited.

According to the present invention, an organopolysiloxane having excellent extensibility and excellent solubility in water and lower alcohols is provided.

Furthermore, a hair cosmetic containing this organopolysiloxane can impart a flexible feel, the set hair is minimally disintegrated even when fingers are passed through the hair or external factors such as wind and vibration are applied, and a natural finish is achieved.

When the hair cosmetic of the present invention contains a specific organic carboxylic acid and a specific organic solvent, it imparts an excellent feel to the hair after application (softness, no greasiness, etc.) without impairing hair reforming effects (improvement of manageability, etc.) of the organic acid and the organic solvent and can further improve styling properties, setting performance and set holding performance. Consequently, there is provided a hair cosmetic that essentially reforms the hair, imparts excellent hair manageability and feel to the touch (softness, no greasiness), and is greatly superior in styling properties, setting performance immediately after getting permed and set holding performance.

Therefore, the hair cosmetic of the present invention is useful particularly as a hair cosmetic such as a hair styling agent and a hair conditioning agent.

In this application, unless stated otherwise, all molecular weight values are molecular weights in units of g/mol as measured by gel permeation chromatography.

Organopolysiloxanes

The organopolysiloxane of the present invention is composed of a poly(N-acylalkyleneimine) segment having a repeating unit represented by the above-mentioned general formula (1) bound to each of at least two silicon atoms in an organopolysiloxane segment as a main chain via an alkylene group containing a hetero atom, as with the organopolysiloxanes described in the above-mentioned JP-A-07-133352, and is characterized in that it causes plastic deformation at extension rates in the range of 0 to 15% and does not break at an extension rate of 300%. In contrast, the organopolysiloxanes described in JP-A-07-133352 do not cause plastic deformation and break under the same conditions. Therefore, the organopolysiloxane of the present invention has properties totally different from those of the organopolysiloxanes described in JP-A-07-133352.

In the present specification, whether plastic deformation occurs at extension rates in the range of 0 to 15% is determined by the following test method. Specifically, a sample section having a thickness of approx. 0.2 mm, a length of 20 mm, and a width of 5 mm is prepared, extended 3 mm (15%) at a crosshead speed of 20 mm/min at a temperature of 20° C. and a relative humidity of 65%, and then immediately the crosshead is returned to the original position at the same speed, while recording a stress-strain curve. Then, 10 minutes later, the sample section is extended again. As a result, when the stress-strain curve at the second extension follows the trajectory of the first curve, it is determined that plastic deformation does not occur. On the other hand, when the stress-strain curve does not follow the same trajectory, it is determined that plastic deformation has occurred. Furthermore, whether a break occurs at an extension rate of 300% is determined based on the appearance of a test sample section having a length of 20 mm a width of 5 mm, and a thickness of 1.0 mm after extending it 300% in the longitudinal direction at an extension speed of 50 mm/min with a tensile tester (Tensilon Tensile Tester, Model RTC-1210A, Orientech Co., Ltd.) at a temperature of 20° C. and a relative humidity 65% and leaving it for 3 min.

The organopolysiloxane of the present invention causes plastic deformation and has high extensibility as described above, and these characteristics are exhibited only by providing structural characteristics of the following i) to iv).

i) A poly(N-acylalkyleneimine) segment binds to at least two silicon atoms in an organopolysiloxane segment as a main chain.

ii) The number-average molecular weight of the poly(N-acylalkyleneimine) segment is 800 to 1600.

iii) The mass ratio (a/b) of the organopolysiloxane segment (a) as a main chain and the poly(N-acylalkyleneimine) segment (b) is 65/35 to 82/18.

iv) The weight-average molecular weight of the organopolysiloxane as a main chain is 10,000 to 100,000.

The poly(N-acylalkyleneimine) segment can bind to at least two arbitrary silicon atoms constituting the organopolysiloxane segment via an alkylene group containing a hetero atom, but preferably binds to one or more silicon atoms that are not either terminus via the above-mentioned alkylene group, more preferably to two or more silicon atoms that are not either terminus via the above-mentioned alkylene group.

The alkylene group containing a hetero atom functions as a linking group of the poly(N-acylalkyleneimine) segment. Examples of the alkylene group include alkylene groups having 2 to 20 carbon atoms which contain 1 to 3 nitrogen atoms, oxygen atoms, or sulfur atoms. Among these, those represented by the following formulas (i) to (vii) are preferable, and those represented by the following formulas (i) and (ii) are more preferable. In the formulas, An⁻ represents a counter ion of a quaternary ammonium salt, and examples thereof include an ethyl sulfate ion, a methyl sulfate ion, a chloride ion, an iodide ion, a sulfate ion, a p-toluenesulfonate ion, and a perchlorate ion.

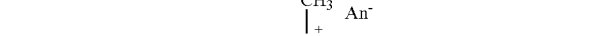

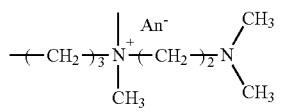

(v)

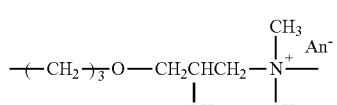

(vi)

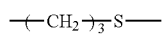

(vii)

The N-acylalkyleneimine unit constituting the poly(N-acylalkyleneimine) segment is represented by the above-mentioned general formula (1). Definitions of the symbols in the formula will be explained below.

Examples of the alkyl group having 1 to 22 carbon atoms for $R^1$ include straight, branched or cyclic alkyl groups each having 1 to 22 carbon atoms, and specific examples thereof include a methyl group, an ethyl group, an n-propyl group, an isopropyl group, an n-butyl group, a tert-butyl group, a pentyl group, a hexyl group, a cyclohexyl group, a heptyl group, an octyl group, a nonyl group, a decyl group, an undecyl group, a dodecyl group, an octadecyl group, a nonadecyl group, an eicosyl group, a docosyl group, and so forth. Among these, alkyl groups having 1 to 10 carbon atoms are preferable, and alkyl groups having 1 to 6 carbon atoms are more preferable.

Examples of the aralkyl group include aralkyl groups having 7 to 15 carbon atoms, and specific examples thereof include a benzyl group, a phenethyl group, a trityl group, a naphthylmethyl group, an anthracenylmethyl group, and so forth. Among these, aralkyl groups having 7 to 14 carbon atoms are preferable, and aralkyl groups having 7 to 10 carbon atoms are more preferable.

Examples of the aryl group include aryl groups having 6 to 14 carbon atoms, and specific examples thereof include a phenyl group, a tolyl group, a xylyl group, a naphthyl group, a biphenyl group, an anthryl group, a phenanthryl group, and so forth. Among these, aryl groups having 6 to 12 carbon atoms are preferable, and aryl groups having 6 to 9 carbon atoms are more preferable.

Among these, alkyl groups having 1 to 6 carbon atoms are even more preferable as $R^1$.

The mass ratio (a/b) of the organopolysiloxane segment (a) and the poly(N-acylalkyleneimine) segment (b) is 65/35 to 82/18, but is preferably 68/32 to 80/20, more preferably 70/30 to 79/21 in view of not breaking and exhibiting plastic deformation even at extension rates of 300% or higher, ensuring sufficient membrane strength, and improving styling properties, setting performance and set holding performance, in use as the hair cosmetic described later.

In the present specification, the mass ratio (a/b) is a value obtained by dissolving 5% by mass of the organopolysiloxane of the present invention in deuterated chloroform and performing a nuclear magnetic resonance ($^1$H-NMR) analysis to obtain the integral ratio of an alkyl group or a phenyl group in the organopolysiloxane segment and a methylene group in the poly(N-acylalkyleneimine) segment.

Furthermore, the weight-average molecular weight (MWg) of an organopolysiloxane segment between adjacent poly(N-acylalkyleneimine) segments is preferably 1500 to 3500, preferably 1600 to 3200, more preferably 1700 to 3000 in view of not breaking and exhibiting plastic deformation even at extension rates of 300% or higher, ensuring sufficient membrane strength, and improving styling properties, setting performance and set holding performance, in use as the hair cosmetic described later.

In the present specification, the "organopolysiloxane segment between adjacent poly(N-acylalkyleneimine) segments" means a segment surrounded by the broken line between two points, the binding point of a poly(N-acylalkyleneimine) segment to an organopolysiloxane segment (binding point α) and the binding point (binding point β) of an adjacent poly(N-acylalkyleneimine) segment, as shown in the following formula (6), which consists of one unit of $R^7SiO$, one $R^{11}$, and y+1 units of $R^7_2SiO$. Furthermore, the "poly(N-acylalkyleneimine) segment" refers to W, which binds to the above-mentioned $R^{11}$.

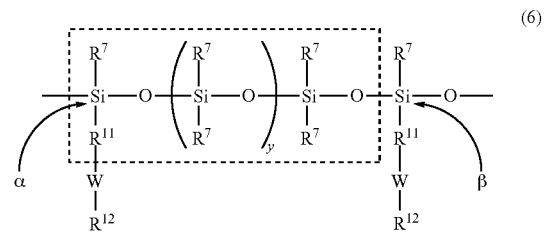

(6)

In the above-mentioned general formula (6), $R^7$ each independently represents an alkyl group or a phenyl group each having 1 to 22 carbon atoms, $R^{11}$ represents an alkylene group containing a hetero atom, W represents a poly(N-acylalkyleneimine) segment, $R^{12}$ represents a residue of a polymerization initiator, and y is a positive number.

MWg is the molecular weight of the portion surrounded by the broken line in the above-mentioned general formula (6) and can be understood as the mass (g/mol) of an organopolysiloxane segment per mole of the poly(N-acylalkyleneimine) segment. When 100% of a functional group of a modified organopolysiloxane, a starting compound, is replaced with poly(N-acylalkyleneimine), the value is equal to the functional group equivalent (g/mol) of the modified organopolysiloxane.

The molecular weight (MWox) of a poly(N-acylalkyleneimine) segment can be measured by a method of calculating from the molecular weight and the polymerization degree of a N-acylalkyleneimine unit or a measuring method by gel permeation chromatography (GPC) described later. In the present invention, the number-average molecular weight is measured by a measuring method by GPC and is preferably 800 to 1600, more preferably 850 to 1500, even more preferably 900 to 1400. Consequently, the organopolysiloxane does not break and plastic deformation is exhibited even at extension rates of 300% or higher, and sufficient membrane strength can be ensured. Furthermore, styling properties, setting performance and set holding performance, can be further improved in use as the hair cosmetic described later.

Furthermore, MWg can be obtained from the following formula (I) using the content percentage (Csi) of an organopolysiloxane segment as a main chain.

$$MWg = \frac{Csi \times MWox}{100 - Csi} \quad (I)$$

The weight-average molecular weight (MWsi) of an organopolysiloxane segment as a main chain is 10,000 to 100,000, preferably 20,000 to 80,000, more preferably 30,000 to 60,000 in view of not breaking and exhibiting plastic deformation at extension rates of 300% or higher, ensuring sufficient membrane strength, and further solubility in polar solvents such as water and easiness to handle after dissolution. To have a skeleton common to that of a modified organopolysiloxane, the starting compound, MWsi is nearly the same as the weight-average molecular weight of the modified organopolysiloxane, the starting compound. The average molecular weight of modified organopolysiloxane, the starting compound, is the polystyrene-equivalent weight-average molecular weight obtained by GPC under the following conditions.

Column: Super HZ4000+Super HZ2000 (Tosoh Corporation)
Eluent: 1 mM triethylamine/THF
Flow rate: 0.35 mL/min
Column temperature: 40° C.
Detector: UV
Sample: 50 µL The weight-average molecular weight (MWt) of the organopolysiloxane of the present invention is preferably 12,000 to 150,000, more preferably 24,000 to 120,000, even more preferably 37,000 to 92,000. Consequently, the organopolysiloxane does not break and plastic deformation exhibited even at extension rates of 300% or higher, sufficient membrane strength can be ensured, and, in addition, excellent solubility in polar solvents such as water is achieved. Furthermore, styling properties, setting performance and set holding performance, can be further improved in use as the hair cosmetic described later. In the present specification, MWt can be obtained from the weight-average molecular weight of a modified organopolysiloxane, the starting compound, and the above-mentioned mass ratio (a/b).

Methods for producing the organopolysiloxane of the present invention will be explained below.

For example, the organopolysiloxane of the present invention is produced by reacting a modified organopolysiloxane represented by the following general formula (7):

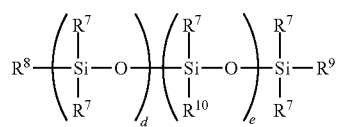

(7)

wherein $R^7$ has the same meaning as defined above, and $R^8$ and $R^9$ each represent a group identical to $R^7$ or a monovalent group represented by any of the following formulas (viii) to (xiii):

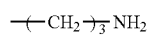

(viii)

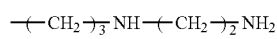

(ix)

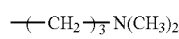

(x)

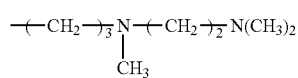

(xi)

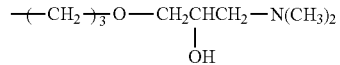

(xii)

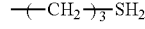

(xiii)

wherein $R^{10}$ represents a monovalent group represented by any of the above-mentioned formulas (viii) to (xiii), d is an integer of 135 to 1350, and e is an integer of 3 to 57) and a terminal reactive poly(N-acylalkyleneimine) obtained by ring-opening polymerization of a cyclic imino ether represented by the following general formula (8):

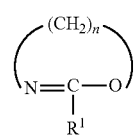

(8)

wherein $R^2$ and n have the same meaning as defined above.

It is desirable to use a modified organopolysiloxane whose functional group equivalent is preferably 1700 to 3500, more preferably 1800 to 3200, even more preferably 2000 to 3000, and whose weight-average molecular weight is preferably 10,000 to 100,000, more preferably 20,000 to 80,000, even more preferably 30,000 to 60,000.

Furthermore, it is desirable to adjust the molecular weight of the terminal reactive poly(N-acylalkyleneimine) to preferably 800 to 1600, more preferably 850 to 1500, even more preferably 900 to 1400.

The ring-opening polymerization of a cyclic imino ether (8) can be performed using a polymerization initiator. Examples of the polymerization initiator include compounds having strong electrophilic reactivity, for example, alkyl esters of strong acids such as alkyl benzenesulfonates, alkyl p-toluenesulfonates, alkyl trifluoromethanesulfonates, alkyl trifluoroacetates, dialkyl sulfates, and the like. Among these, dialkyl sulfates are preferably used. The amount of the polymerization initiator used is usually 1 mol based on 2 to 100 mol of a cyclic imino ether (8).

Examples of the polymerization solvent include acetic acid esters such as ethyl acetate and propyl acetate, ethers such as diethyl ether, diisopropyl ether, dioxane, and tetrahydrofuran, ketones such as acetone and methyl ethyl ketone, halogen solvents such as chloroform and methylene chloride, nitrile solvents such as acetonitrile and benzonitrile, and aprotonic polar solvents such as N,N-dimethylformamide, N,N-dimethylacetamide, and dimethyl sulfoxide. Among these, acetic acid esters are preferably used. The amount of a solvent used is usually 20 to 2000 parts by mass based on 100 parts by mass of a cyclic imino ether (8).

The polymerization temperature is usually 30 to 170° C., preferably 40 to 150° C. The polymerization time is not uniform depending on the polymerization temperature and the like, but is usually 1 to 60 h.

When a 2-substituted-2-oxazoline is used as a cyclic imino ether (8), for example, poly(N-acylethyleneimine) with n=2 in the above-mentioned general formula (1) is obtained. When a 2-substituted-dihydro-2-oxazine is used, poly(N-acylpropyleneimine) with n=3 in the above-mentioned general formula (1) is obtained.

Examples of the method for linking poly(N-acylalkyleneimine) and an organopolysiloxane segment include the following methods.

1) A method of reacting a modified organopolysiloxane represented by the above-mentioned general formula (7) with a terminal reactive poly(N-acylalkyleneimine) obtained by living polymerization of a cyclic imino ether
2) Formation reaction of an ester by condensation of a carboxyl group and a hydroxy group
3) Formation reaction of an amide by condensation of a carboxyl group and an amino group
4) Formation reaction of a secondary, tertiary, or quaternary ammonium from a halogenated alkyl group and a primary, secondary, or tertiary amino group
5) Addition reaction of a vinyl group to an Si—H group of an organopolysiloxane
6) Formation reaction of a β-hydroxy amine from an epoxy group and an amino group Among these, the method of the above-mentioned 1) is most effective in that the degree of polymerization can be easily regulated by the amounts of a cyclic imino ether (8) and a polymerization initiator used as shown in the following theoretical formula (II) [MWi, molecular weight of poly(N-acylpropyleneimine)], and that nearly-monodispersed poly(N-acylalkyleneimine) with a narrower molecular weight distribution than in usual radical polymerization can be obtained.

$$Mwi = \frac{\text{Number of moles of cyclic imino ether}}{\text{Number of moles of polymerization initiator}} \times \text{Molecular weight of cyclic imino ether} + \text{Molecular weight of polymerization initiator} \qquad (II)$$

The organopolysiloxane of the present invention has a unique structure in which a poly(N-acylalkyleneimine) segment binds to at least two silicon atoms of an organopolysiloxane segment having a predetermined molecular weight via an alkylene group containing a hetero atom at a predetermined interval and a predetermined ratio. Consequently, the organopolysiloxane of the present invention is suitably added to a hair cosmetic since plastic deformation is exhibited, both high extensibility and high membrane strength are achieved, and it can be dissolved in polar solvents such as water and lower alcohols.

Examples of the organopolysiloxane of the present invention include poly(N-formylethyleneimine)organosiloxane, poly(N-acetylethyleneimine)organosiloxane, poly(N-propionylethyleneimine)organosiloxane, and so forth.

Hair Cosmetic

The hair cosmetic of the present invention is characterized in that the organopolysiloxane of the present invention described above is contained. Consequently, a flexible feel, setting performance that the hair style is not disintegrated after passing fingers through hair, and a more natural finish can be obtained.

The organopolysiloxane of the present invention can be used solely or two or more thereof can be used in combination. The content thereof is preferably 0.05 to 20% by mass, more preferably 0.1 to 15% by mass, even more preferably 0.1 to 10% by mass, even more preferably 0.5 to 5% by mass based on the total mass of the hair cosmetic in view of hair setting performance, set holding performance, and wash property by shampooing. Furthermore, with such contents, when organic solvents and organic acids or salts thereof described later are used in combination, styling properties, setting performance and set holding performance, can be further improved without impairing hair reforming effects (improvement of manageability, etc.) of the organic acids and the organic solvents.

Furthermore, the hair cosmetic of the present invention can further contain an organic solvent selected from the following (b1) to (b5) (hereinafter, referred to as "component (B)") as a preferred component.

(b1) Compound represented by general formula (2)

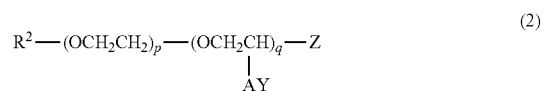

wherein $R^2$ represents a hydrogen atom, an alkyl group having 1 to 6 carbon atoms or a group $R^3$-Ph-$R^4$— (wherein $R^3$ represents a hydrogen atom, a methyl group, or a methoxy group; $R^4$ represents a bond or a saturated or unsaturated divalent hydrocarbon group having 1 to 3 carbon atoms; and Ph represents a paraphenylene group), A represents a bond or a saturated divalent hydrocarbon group having 1 to 4 carbon atoms, Y and Z each independently represent a hydrogen atom or a hydroxy group, and p and q are each independently an integer of 0 to 5, provided that when p=q=0, Z represents a hydroxy group, and $R^2$ is not either a hydrogen atom or a group $R^3$-Ph-;

(b2) N-alkylpyrrolidone or N-alkenylpyrrolidone in which an alkyl group or an alkenyl group having 1 to 18 carbon atoms binds to a nitrogen atom;
(b3) Alkylene carbonate having 2 to 4 carbon atoms;
(b4) Polypropylene glycol having a number-average molecular weight of 100 to 1000; and
(b5) Lactone or cyclic ketone represented by the following general formula (3), (4), or (5)

wherein X represents a methylene group or an oxygen atom, $R^5$ and $R^6$ represent different substituents, and a and b are each independently 0 or 1.

Among the organic solvents, components (B), examples of (b1) include straight or branched C1 to C6 lower alcohols such as ethanol, isopropanol, butanol, and isobutanol, ethylene glycol, propylene glycol, dipropylene glycol, 1,3-butane diol, benzyl alcohol, cinnamyl alcohol, phenethyl alcohol, p-anisyl alcohol, p-methylbenzyl alcohol, phenoxyethanol, 2-benzyloxyethanol, methylcarbitol, ethylcarbitol, propylcarbitol, butylcarbitol, triethylene glycol monoethyl ether, triethylene glycol monobutyl ether, and so forth.

Examples of (b2) include N-methylpyrrolidone, N-octylpyrrolidone, N-laurylpyrrolidone, and so forth.

Examples of (b3) include ethylene carbonate, propylene carbonate, and so forth.

As the polypropylene glycol having a number-average molecular weight of 100 to 1000, (b4), those having a number-average molecular weight of 300 to 500 are preferable. Here, the number-average molecular weight means a number-average molecular weight in terms of polystyrene measured by GPC.

In (b5), preferable examples of $R^5$ and $R^6$ in the general formulas (3) to (5) include straight, branched, or cyclic alkyl groups, a hydroxy group, a sulfonate group, a phosphate group, a carboxy group, a phenyl group, a sulfoalkyl group, an alkyl phosphate group, a carboxyalkyl group, and so forth. Among these, straight or branched alkyl groups having 1 to 6 carbon atoms, for example, a methyl group, an ethyl group, a propyl group, an isopropyl group, and a butyl group are preferable. These groups are preferably substituted at the γ-position in γ-lactone and at the δ-position in δ-lactone (specifically, methylene adjacent to a heterooxygen atom). Furthermore, when water-solubility of compounds (3) to (5) needs to be increased, these compounds preferably have an acidic group such as a sulfonate group, a phosphate group, and a carboxy group or an alkyl group substituted by these groups as $R^5$ or $R^6$. Among (b5), examples of lactones include γ-butyrolactone, γ-caprolactone, γ-valerolactone, δ-valerolactone, δ-caprolactone, δ-heptanolactone, and so forth. In view of stability of lactone, γ-lactone, in particular, γ-butyrolactone and γ-caprolactone are preferable. Among (b5), examples of cyclic ketones include cyclopentanone, cyclohexanone, cycloheptanone, 4-methylcycloheptanone, and so forth.

Furthermore, the component (B) used in the present invention is preferably liquid at 25° C., and C log P is preferably −2 to 3, more preferably −1 to 2 in view of penetration enhancement. Here, C log P is an octanol-water-distribution coefficient (log P) defined by the following formula (III), a measure of distribution of a substance between the octanol phase and the aqueous phase, and an example thereof is described in Chemical Reviews, Vol. 71, No. 6 (1971).

$$\log P = \log([\text{substance}]_{Octanol}/[\text{substance}]_{Water}) \quad \text{(III)}$$

wherein [substance]$_{Octanol}$ represents a molar concentration of a substance in the 1-octanol phase, and [substance]$_{Water}$ Represents a Molar Concentration of the substance in the aqueous phase.

Specific C log P of the representative components (B) are dipropylene glycol (−0.67), 1,3-butanediol (−0.29), benzyl alcohol (1.1), 2-benzyloxyethanol (1.2), 2-phenylethanol (1.2), 1-phenoxy-2-propanol (1.1), polypropylene glycol 400 (0.9), propylene carbonate (−0.41), and γ-butyrolactone (−0.64).

Two or more of components (B) may be used in combination, and the total content thereof is preferably 0.1 to 40% by mass of the hair cosmetic of the present invention, more preferably 0.5 to 10% by mass, even more preferably 1 to 5% by mass in view of effects of improving firmness and body after shampooing, effects of improving softness and manageability of the hair, and promotion of reforming effects (improvement of elasticity and moisture resistance, etc.).

Furthermore, the hair cosmetic of the present invention can contain water or a straight or branched saturated or unsaturated C1 to C6 alcohol as a solvent in view of hair setting performance, favorable usability, and promotion of solubility during the preparation of a hair cosmetic. The solvent can be used solely, or two or more thereof can be used in combination. Among these, water and C1 to C6 lower alcohols such as ethanol and isopropanol are preferable, and water and ethanol are more preferable. The total content of water and alcohols is preferably 0.1 to 98% by mass of the total mass of a hair cosmetic, more preferably 1 to 90% by mass, even more preferably 5 to 60% by mass.

Furthermore, the hair cosmetic of the present invention can contain an organic carboxylic acid or a salt thereof (hereinafter, referred to as "component (A)") that may have a hydroxy group, together with a component (B). In this case, particularly preferable examples of the component (B) include dipropylene glycol, 1,3-butane diol, benzyl alcohol, phenoxyethanol, 2-benzyloxyethanol, propylene carbonate, and polypropylene glycol (a number-average molecular weight of 300 to 500, more preferably 400).

Organic carboxylic acids having 2 to 8 carbon atoms are preferable as components (A), and specific examples thereof include monocarboxylic acids such as acetic acid and propionic acid, dicarboxylic acids such as malonic acid, succinic acid, glutaric acid, adipic acid, maleic acid, fumaric acid, and phthalic acid, polycarboxylic acids such as polyglutamic acid, hydroxycarboxylic acids such as glycolic acid, lactic acid, hydroxyacrylic acid, glyceric acid, malic acid, tartaric acid, and citric acid, acidic amino acids such as glutamic acid and aspartic acid, and so forth. Among these, hydroxycarboxylic acids having 2 to 6 carbon atoms are preferable, and lactic acid and malic acid are more preferable. Examples salts of these organic carboxylic acids include salts with alkali metals, alkaline earth metals, ammonia, and organic amine compounds.

Two or more of these components (A) may be used in combination, and the total content thereof is preferably 0.1 to 30% by mass of the hair cosmetic of the present invention, more preferably 0.5 to 20% by mass, even more preferably 0.5 to 10% by mass in view of effects of reforming the inside of the hair (repairing hollows, etc.), effects of improving firmness and body after shampooing, and effects of improving softness and manageability of the hair.

The mass ratio of an organic carboxylic acid or a salt thereof as component (A) and an organic solvent as component (B) is preferably in the range of (A):(B)=10:1 to 1:7, more preferably 4:1 to 1:3 to effectively exhibit effects of reforming the inside of the hair (repairing hollows, etc.), effects of improving firmness and body after shampooing, and effects of improving softness and manageability of the hair.

Furthermore, when a set polymer is added to the hair cosmetic of the present invention, the set holding performance is further improved, and the smooth feel of the hair becomes favorable.

Examples of the set polymer include those shown in the following 1) to 8). These polymers can be used solely, or two or more thereof can be used in combination.

1) Vinylpyrrolidone Polymers

Polyvinylpyrrolidones

Examples thereof include marketed products such as Luviskol K12 and K30 (BASF) and PVP K15 and K30 (GAF Corporation).

Vinylpyrrolidone/Vinyl Acetate Copolymers

Examples thereof include marketed products such as Luviskol VA28 and VA73 (BASF) and PVP/VA E-735 and S-630 (GAF Corporation).

Vinylpyrrolidone/Vinyl Acetate/Vinyl Propionate Ternary Copolymer

Examples thereof include marketed products such as Luviskol VAP343 (BASF).

Vinylpyrrolidone/Alkyl Aminoacrylate Copolymer

Examples thereof include marketed products such as Luviflex (BASF) and copolymers 845, 937, and 958 (GAF Corporation).

Vinylpyrrolidone/Acrylate/(Meth)Acrylic Acid Copolymer

Examples thereof include marketed products such as Luviflex VBM35 (BASF).

Vinylpyrrolidone/Alkyl Aminoacrylate/Vinyl Caprolactam Copolymer

Examples thereof include marketed products such as copolymer VC-713 (GAF Corporation).

2) Acidic Vinyl Ether Polymers

Methyl Vinyl Ether/Maleic Anhydride Alkyl Half-Ester Copolymers

Examples thereof include marketed products such as Gantrez ES-225, ES-425, and SP-215 (GAF Corporation).

3) Acidic Polyvinyl Acetate Polymers

Vinyl Acetate/Crotonic Acid Copolymers

Examples thereof include marketed products such as resin 28-1310 (National Starch and Chemical Company) and Luviset CA66 (BASF).

Vinyl Acetate/Crotonic Acid/Vinyl Neodecanoate Copolymer

Examples thereof include marketed products such as resin 28-2930 (National Starch and Chemical Company).

Vinyl Acetate/Crotonic Acid/Vinyl Propionate Copolymers

Examples thereof include marketed products such as Luviset CAP (BASF).

4) Acidic Acrylic Polymers (Meth)Acrylate/(Meth)Acrylate Ester Copolymers

Examples thereof include marketed products such as Plus Size L53P (Goo Chemical Co., Ltd.) and Diahold (Mitsubishi Petrochemical Co., Ltd.).

Acrylate/Alkyl Acrylate Ester/Alkyl Acrylamide Copolymers

Examples thereof include marketed products such as Ultra Hold 8 (BASF) and Unfoamer V-42 (National Starch and Chemical Company).

5) Ampholytic Acrylic Polymers (Meth)Acryl Ethyl Betaine/Alkyl(Meth)Acrylate Copolymers Examples thereof include copolymers of N-methacryloyloxyethyl-N,N-dimethylammonium-α-N-methylcarboxybetaine and alkyl (meth)acrylate, for example, marketed products such as Yukafoamer M-75, SM (Mitsubishi Petrochemical Co., Ltd.).

Alkyl Acrylate/Butylaminoethyl Methacrylate/Octyl Acrylate Amide Copolymers

Examples thereof include octyl acrylamide/acrylate/butylaminoethyl methacrylate copolymers, for example, marketed products such as Unfoamer 28-4910 (National Starch and Chemical Company).

6) Basic Acrylic Polymers

Acrylamide Acryl Ester Copolymers

Examples thereof include those in the examples of JP-A-02-180911 and JP-A-08-291206.

7) Cellulose derivatives

Cationic Cellulose Derivatives

Examples thereof include marketed products such as Celquat H-100, L-200 (National Starch and Chemical Company).

8) Chitin or Chitosan Derivatives

Hydroxypropyl Chitosan

Examples thereof include marketed products such as Chitofilmer (Ichimaru Pharcos Co., Ltd.).

Salts of carboxymethyl chitin, carboxymethyl chitosan, chitosan with monovalent acids such as pyrrolidonecarboxylic acid, lactic acid, and glycolic acid or with divalent acids such as adipic acid and succinic acid Examples thereof include marketed products such as Chitomer PC (pyrrolidonecarboxylic acid salt) and Chitomer L (lactic acid salt) (Union Carbide).

Among these set polymers, set polymers selected from acrylic polymers and vinylpyrrolidone polymers are particularly preferable. The content of a set polymer is preferably 0.05 to 20% by mass of the total mass of a hair cosmetic, more preferably 0.1 to 10% by mass, even more preferably 0.3 to 5% by mass.

To further improve the conditioning effect, the hair cosmetic of the present invention can contain an oil solution and a conditioning component selected from silicones other than the above-mentioned organopolysiloxanes.

Oil solutions are used to improve manageability and the feeling of dried hair. Examples of oil solutions include hydrocarbons such as squalene, squalane, liquid isoparaffin, light liquid isoparaffin, heavy liquid isoparaffin, α-olefin oligomers, liquid paraffin, and cycloparaffin, glycerides such as caster oil, cacao oil, mink oil, avocado oil, and olive oil, waxes such as beeswax, spermaceti, lanolin, microcrystalline wax, ceresin wax, and carunauba wax; higher alcohols such as cetyl alcohol, oleyl alcohol, stearyl alcohol, isostearyl alcohol, and 2-octyldodecanol, esters such as octyldodecyl myristate, hexyl laurate, cetyl lactate, monostearate propylene glycol, oleyl oleate, hexadecyl 2-ethylhexanoate, isononyl isononanoate, and tridecyl isononanoate, higher fatty acids such as caprynic acid, lauric acid, myristic acid, palmitic acid, stearic acid, behenic acid, oleic acid, coconut oil fatty acids, isostearylic acid, and isopalmitic acid, solid fats such as cholesterol, Vaseline, cholesteryl isostearate, and sphingo lipid, as well as jojoba oil, isostearyl glyceryl ether, polyoxypropylene butyl ether, and so forth. Among these, branched hydrocarbons such as squalene, squalane, liquid isoparaffin, light liquid isoparaffin, heavy liquid isoparaffin, and α-olefin oligomers are particularly preferable.

The content of an oil solution is preferably 0.05 to 20% by mass of the hair cosmetic of the present invention, more preferably 0.1 to 10% by mass, even more preferably 0.5 to 5% by mass in view of favorable manageability and no greasiness.

Examples of silicones include dimethyl polysiloxane, polyether-modified silicones, amino-modified silicones, carboxy-modified silicones, methylphenylpolysiloxane, fatty acid-modified silicones, alcohol-modified silicones, aliphatic alcohol-modified silicones, epoxy-modified silicones, fluorine-modified silicones, cyclic silicones, alkyl-modified silicones, and so forth. Among these, dimethylpolysiloxane, polyether-modified silicones, and amino-modified silicones are preferable.

Dimethylpolysiloxane can impart a favorable lubricating property to the hair, polyether-modified silicones can impart smoothness to the hair, and amino-modified silicones can impart a moistening feel to hair. In the present invention, various silicones can be used solely, or two or more thereof can be used in combination depending on the required performance.

Dimethylpolysiloxane having a viscosity of approx. 5 mm$^2$/s to approx. 10,000,000 mm$^2$/s often provided as emulsifiers can be used depending on the required feel, and those having a viscosity of 5000 to 10,000,000 mm$^2$/s, particularly a viscosity of 50,000 to 10,000,000 mm$^2$/s are preferable.

Polyether-modified silicones are not limited so long as they are silicones having a polyoxyalkylene group, and examples of groups constituting the polyoxyalkylene group include an oxyethylene group and an oxypropylene group. More specific examples thereof include KF-6015, KF-945A, KF-6005, KF-6009, KF-6013, KF-6019, KF-6029, KF-6017, KF-6043, KF-353A, KF-354A, and KF-355A (Shin-Etsu Chemical Co., Ltd.), FZ-2404, SS-2805, FZ-2411, FZ-2412, SH3771M, SH3772M, SH3773M, SH3775M, SH3749, SS-280X series, BY22-008M, BY11-030, and BY25-337 (Dow Corning Toray Co., Ltd.), and so forth.

Amino-modified silicones having an average molecular weight of approx. 3000 to 100,000, described under the name of amodimethicone in the Cosmetic, Toiletry and Fragrance Association (CTFA) Dictionary (U.S., Cosmetic Ingredient Dictionary) 3rd Edition are preferable. Examples thereof include marketed products such as SM 8704C (Dow Corning Toray Co., Ltd.), DC 929 (Dow Corning Corporation), KT 1989 (GE Toshiba Silicones), 8500 Conditioning Agent, DOW CORNING TORAY SS-3588, DOW CORNING TORAY SILSTYLE 104 (Dow Corning Toray Co., Ltd.), and so forth.

The content of silicones is preferably 0.05 to 20% by mass of the hair cosmetic of the present invention, more preferably 0.1 to 10% by mass, even more preferably 0.5 to 5% by mass in view of the finger passing property and no greasiness.

The hair cosmetic of the present invention can contain a surfactant in view of the system stability including solubility, dispersibility, and the like of a solvent and improvement of the feel. As a surfactant, any of cationic surfactants, nonionic surfactants, ampholytic surfactants, and anionic surfactants can be used.

Examples of cationic surfactants include quaternary ammonium salts represented by the following general formula (9):

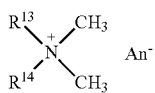

(9)

wherein $R^{13}$ and $R^{14}$ each independently represent a hydrogen atom or an alkyl group or a benzyl group having 1 to 28 carbon atoms and are not a hydrogen atom, a benzyl group, or a lower alkyl group having 1 to 3 carbon atoms or any combination thereof at the same time, and An$^-$ has the same meaning as defined above.

Here, one of $R^{13}$ and $R^{14}$ represents preferably an alkyl group having 16 to 24 carbon atoms, more preferably having 22 carbon atoms, even more preferably a straight alkyl group, and the other one preferably represents a lower alkyl group having 1 to 3 carbon atoms, more preferably a methyl group.

As cationic surfactants, mono-long chain alkyl quaternary ammonium salts are preferable, and specific examples thereof include cetyltrimethyl ammonium chloride, stearyltrimethyl ammonium chloride, alkyltrimethyl ammonium chloride, behenyltrimethyl ammonium chloride, alkyl benzalkonium chloride, and so forth. Stearyltrimethyl ammonium chloride and behenyltrimethyl ammonium chloride are particularly preferable.

Examples of nonionic surfactants include polyoxyalkylene alkyl ethers, polyoxyalkylene alkenyl ethers, higher fatty acid sucrose esters, polyglycerine fatty acid esters, higher fatty acid mono or diethanol amides, polyoxyethylene hydrogenated caster oil, polyoxyethylene sorbitan fatty acid esters, polyoxyethylene sorbit fatty acid esters, alkyl saccharide surfactants, alkyl amine oxides, alkyl amide amine oxides, and so forth. Among these, polyoxyalkylene alkyl ether and polyoxyethylene hydrogenated caster oil are preferable, and polyoxyethylene alkyl ethers and polyoxyethylene·polyoxypropylene alkyl ethers are particularly preferable.

Examples of ampholytic surfactants include imidazoline surfactants, carbobetaine surfactants, amidobetaine surfactants, sulfobetaine surfactants, hydroxysulfobetaine surfactants, amidosulfobetaine surfactants, and so forth. Among these, betaine surfactants such as alkyl dimethyl aminoacetic acid betaines and fatty acid amidopropyl betaines are preferable, and fatty acid amidopropyl betaines are more preferable. Fatty acid amidopropyl betaines having 8 to 18 carbon atoms, in particular, those containing an acyl group having 10 to 16 carbon atoms are preferable. More preferable examples thereof include lauric acid amidopropyl betaines, palm kernel oil fatty acid amidopropyl betaines, coconut oil fatty acid amidopropyl betaines, and so forth.

Examples of anionic surfactants include alkylbenzenesulfonates, alkyl or alkenyl ether sulfates, alkyl or alkenyl sulfuric acid salts, olefinsulfonates, alkanesulfonates, saturated or unsaturated fatty acid salts, alkyl or alkenyl ether carboxylic acid salts, α-sulfone fatty acid salts, N-acylamino acid surfactants, phosphate mono or diester surfactants, sulfosuccinic acid esters, and so forth. Examples of counter ions of anionic residues of the above-mentioned surfactants include alkali metal ions such as a sodium ion and a potassium ion, alkaline earth metal ions such as a calcium ion and a magnesium ion, an ammonium ion, and alkanol amine containing 1 to 3 alkanol groups having 2 or 3 carbon atoms (for example, monoethanolamine, diethanolamine, triethanolamine, triisopropanolamine, etc.). Furthermore, examples of counter ions of cationic residues include halide ions such as a chloride ion, a bromide ion, and an iodide ion, a methosulfate ion, and a saccharinate ion.

Among these, cationic surfactants and nonionic surfactants are preferable in view of its feel to the touch. Surfactants can be used solely, or two or more thereof can be used in combination. In view of the system stability including solubilization of a solvent and emulsification of an oil solution, the content is preferably 0.01 to 10% by mass, more preferably 0.05 to 5% by mass of the hair cosmetic of the present invention.

Furthermore, the hair cosmetic of the present invention can contain polyhydric alcohols other than components (B). Polyhydric alcohols contribute to solubilization and stable distribution of components (B) and act synergistically with components (B) to promote improvement of luster and hair reforming effects. Examples of the polyhydric alcohols include ethylene glycol, glycerine, and sorbitol, and glycerine is particularly preferable. Polyhydric alcohols can be used solely, or two or more thereof can be used in combination. The content thereof is preferably 0.1 to 10% by mass, more preferably 0.5 to 5% by mass in the hair cosmetic of the present invention.

In addition to the above-mentioned components, components usually used in hair cosmetics can be suitably mixed in the hair cosmetic of the present invention depending on the objective, purpose, form, and the like. Examples of such components include anti-dandruff agents such as zinc pyrithione and octopirox, vitamin agents, disinfectants such as triclosan and trichlorocarban, anti-inflammatory agents such as dipotassium glycyrrhizinate and tocopherol acetate, preservatives such as methylparaben and butylparaben, chelating agents, moisturizing agents such as panthenol, coloring materials such as dyes and pigments, viscosity modifiers such as hydroxyethylcellulose, methylcellulose, polyethylene glycol, and clay minerals, organic acids other than components (A), pH modifiers such as sodium hydroxide and potassium hydroxide, plant extracts, pearlescents, perfumes, coloring matters, ultraviolet absorbers, antioxidants, and other components described in Encyclopedia of Shampoo Ingredients (Micelle Press).

The hair cosmetic of the present invention can be prepared in various forms by usual methods, for example, not only in liquid compositions such as mists, lotions, and tonics but also in semisolid compositions such as gels, pastes, creams, and waxes. Liquid compositions using water and/or a lower alcohol, in particular, water and a lower C1 to C3 alcohol as a solvent are preferable. Examples of such lower alcohols include ethanol, 1-propanol, 2-propanol, and so forth, and, among these, ethanol is preferable.

By suitably selecting a form and mixed components depending on the purpose, for example, the hair cosmetic of the present invention can be prepared as shampoo compositions, hair conditioning compositions, and further semisolid styling compositions.

Measures for applying these hair cosmetics to the hair are not uniform depending on the form, but usually jetting such as spraying, application by hand, a combination thereof, and the like are employed. Furthermore, a solvent after application is preferably removed by natural drying, heating, or the like. To set the hair in a desired shape, it is desirable to shape the hair before drying after application. Shaping is performed usually by a method using a brush, a dryer, a flat iron, or a curler or the like.

Furthermore, a propellant may be added to the hair cosmetic of the present invention to prepare an aerosol hair cosmetic. The propellants are not particularly limited, so long as they are usually used in aerosol-type cosmetics, and examples thereof include saturated lower hydrocarbons such as propane, butane, or mixtures thereof (including a liquefied petroleum gas), ethers such as dimethyl ether, a nitrogen gas, carbon dioxide, a nitrous oxide gas, and so forth. These can be used solely, or two or more thereof can be used in combination. The content of a propellant is preferably 0.01 to 50% by mass of the hair cosmetic of the present invention, more preferably 5 to 20% by mass.

Furthermore, the hair cosmetic of the present invention can be prepared as a non-aerosol-type hair cosmetic by filling a composition containing the above-mentioned organopolysiloxane and components (A) and (B) in a foam discharge container. The foam discharge containers are not particularly limited, so long as the composition is mixed with air and discharged as a foam. Examples thereof include squeeze foamers, which are used by pressing the body of a soft container with fingers, pump foamers, which have a pump mechanism and are used by pressing the head of the cap with a finger, trigger types, and so forth.

Examples of squeeze foamers includes those described in JP-Y2-62-042785, JP-Y2-62-042786, and JP-Y2-62-042787 and those similar thereto. Examples of pump foamers include those described in JP-A-07-315463 and JP-A-08-230961 and those similar thereto. These containers are often provided with a mesh body at the discharge port to improve the quality of foam. Among these, those provided with one or two mesh bodies having 100 to 300 meshes are preferable.

Such hair cosmetics are preferably used as hair styling agents, hair conditioning agents, and the like. As the form thereof, pump spray, aerosol spray, pump foam, aerosol foam, gel, lotion, mist, cream, and the like are preferable. Among these, pump spray, pump foam, and aerosol foam are preferable.

Furthermore, after application of the above-mentioned organopolysiloxane containing components (A) and (B) to the hair, penetration of components (A) and (B) into the hair can be promoted by heating a hair cosmetic. Heating can be performed by using a hair iron, a dryer, a heater, a hair singer, or the like. The temperature is preferably 60° C. or higher, more preferably 70° C. or higher.

Furthermore, in everyday life, by treating the hair with the hair cosmetic of the present invention at least once daily and continuing the treatment for preferably 7 days or longer, more preferably 14 days or longer, softness and manageability of the hair and styling properties, setting performance and set holding performance, can be improved.

EXAMPLES

Hereafter, the present invention will be explained specifically with reference to the examples. However, the scope of the present invention is not limited to these examples. In the following examples, the content percentage of an organopolysiloxane segment is a value obtained by the nuclear magnetic resonance method ($^1$H-NMR), and a weight-average molecular weight of the final product is a calculated value. The molecular weight of poly(N-propionylethyleneimine) is a number-average molecular weight obtained by gel permeation chromatography (GPC).
Column: K-804L K-804L, Showa Denko K.K.
Eluent: 1 mmol/L FARMIN DM20 (Kao Corporation)/chloroform
Flow rate: 1.0 mL/min
Column temperature: 40° C.
Detector: RI
Sample amount: 5 mg/mL, 100 μL
In terms of polystyrene Example 1

8.1 g (0.053 mol) of diethyl sulfate and 45.8 g (0.48 mol) of 2-ethyl-2-oxazoline were dissolved in 115 g of dehydrated ethyl acetate, and the mixture was heated to reflux for 8 hours under a nitrogen atmosphere to synthesize a terminal reactive poly(N-propionylethyleneimine). The number-average molecular weight was 1400 by GPC. A solution of 100 g of side-chain primary aminopropyl-modified polydimethylsiloxane (weight-average molecular weight, 32,000; amine equivalent, 2000) in 33% ethyl acetate was added to the mixture in a batch, and the mixture was heated to reflux for 10 hours. The reaction mixture was vacuum concentrated to obtain an N-propionylethyleneimine-dimethylsiloxane copolymer as a light yellow rubber-like semisolid (150 g, yield 97%). The content percentage of an organopolysiloxane segment in the final product was 65% by mass, and the weight-average molecular weight was 49,000. Neutralization titration with hydrochloric acid using methanol as a solvent showed that no amino group remained.

Example 2

By the same method as in Example 1, poly(N-propionylethyleneimine) having a number-average molecular weight of 1100 was obtained from 9.3 g (0.060 mol) of diethyl sulfate, 37.8 g (0.40 mol) of 2-ethyl-2-oxazoline, and 100 g of dehydrated ethyl acetate. Further, using 100 g of a side-chain primary aminopropyl-modified polydimethylsiloxane (weight-average molecular weight, 32,000; amine equivalent, 1750), an N-propionylethyleneimine-dimethylsiloxane copolymer was obtained as a light yellow rubber-like semisolid (141 g, yield 96%). The content percentage of an organopolysiloxane segment in the final product was 68% by mass, and the weight-average molecular weight was 47,000. Neutralization titration with hydrochloric acid using methanol as a solvent showed that no amino group remained.

Example 3

By the same method as in Example 1, poly(N-propionylethyleneimine) having a number-average molecular weight of 1400 was obtained from 6.5 g (0.042 mol) of diethyl sulfate, 36.4 g (0.39 mol) of 2-ethyl-2-oxazoline, and 91 g of dehydrated ethyl acetate. Further, using 100 g of a side-chain primary aminopropyl-modified polydimethylsiloxane (weight-average molecular weight, 20,000; amine equivalent 2500), an N-propionylethyleneimine-dimethylsiloxane copolymer was obtained as a light yellow rubber-like semisolid (137 g, yield 96%). The content percentage of an organopolysiloxane segment in the final product was 70% by mass, and the weight-average molecular weight was 29,000. Neutralization titration with hydrochloric acid using methanol as a solvent showed that no amino group remained.

Example 4

By the same method as in Example 1, poly(N-propionylethyleneimine) having a number-average molecular weight of 1300 was obtained from 6.5 g (0.042 mol) of diethyl sulfate, 34.4 g (0.36 mol) of 2-ethyl-2-oxazoline, and 87 g of dehydrated ethyl acetate. Further, using 100 g of a side-chain primary aminopropyl-modified polydimethylsiloxane (weight-average molecular weight, 40,000; amine equivalent, 2500), an N-propionylethyleneimine-dimethylsiloxane copolymer was obtained as a light yellow rubber-like semisolid (138 g, yield 98%). The content percentage of an organopolysiloxane segment in the final product was 71% by mass, and the weight-average molecular weight was 56,000. Neutralization titration with hydrochloric acid using methanol as a solvent showed that no amino group remained.

Example 5

By the same method as in Example 1, poly(N-propionylethyleneimine) having a number-average molecular weight of 900 was obtained from 6.2 g (0.040 mol) of diethyl sulfate, 20.4 g (0.22 mol) of 2-ethyl-2-oxazoline, and 57 g of dehydrated ethyl acetate. Further, using 100 g of a side-chain primary aminopropyl-modified polydimethylsiloxane (weight-average molecular weight, 35,000; amine equivalent, 2600), an N-propionylethyleneimine-dimethylsiloxane copolymer was obtained as a light yellow viscous semisolid (123 g, yield 97%). The content percentage of an organopolysiloxane segment in the final product was 79% by mass, and the weight-average molecular weight was 51,000. Neutralization titration with hydrochloric acid using methanol as a solvent showed that no amino group remained.

Example 6

By the same method as in Example 1, poly(N-propionylethyleneimine) having a number-average molecular weight of 1200 was obtained from 8.1 g (0.053 mol) of diethyl sulfate, 39.0 g (0.41 mol) of 2-ethyl-2-oxazoline, and 100 g of dehydrated ethyl acetate. Further, using 100 g of a side-chain primary aminopropyl-modified polydimethylsiloxane (weight-average molecular weight, 32,000; amine equivalent, 2000), an N-propionylethyleneimine-dimethylsiloxane copolymer was obtained as a light yellow rubber-like semisolid (143 g, yield 97%). The content percentage of an organopolysiloxane segment in the final product was 68% by mass, and the weight-average molecular weight was 46,000. Neutralization titration with hydrochloric acid using methanol as a solvent showed that no amino group remained.

Example 7

By the same method as in Example 1, poly(N-propionylethyleneimine) having a number-average molecular weight of 1000 was obtained from 4.6 g (0.030 mol) of diethyl sulfate, 17.3 g (0.18 mol) of 2-ethyl-2-oxazoline, and 47 g of dehydrated ethyl acetate. Further, using 100 g of a side-chain primary aminopropyl-modified polydimethylsiloxane (weight-average molecular weight, 65,000; amine equivalent, 3500), an N-propionylethyleneimine-dimethylsiloxane copolymer was obtained as a light yellow viscous semisolid (118 g, yield 97%). The content percentage of an organopolysiloxane segment in the final product was 82% by mass, and the weight-average molecular weight was 79,000. Neutralization titration with hydrochloric acid using methanol as a solvent showed that no amino group remained.

Example 8

By the same method as in Example 1, poly(N-propionylethyleneimine) having a number-average molecular weight of 1500 was obtained from 4.6 g (0.030 mol) of diethyl sulfate, 28.7 g (0.30 mol) of 2-ethyl-2-oxazoline, and 71 g of dehydrated ethyl acetate. Further, using 100 g of a side-chain primary aminopropyl-modified polydimethylsiloxane (weight-average molecular weight 37,000, amine equivalent 3500), an N-propionylethyleneimine-dimethylsiloxane copolymer was obtained as a light yellow viscous semisolid (129 g, yield 97%). The content percentage of an organopolysiloxane segment in the final product was 75% by mass, and the weight-average molecular weight was 49,000. Neutralization titration with hydrochloric acid using methanol as a solvent showed that no amino group remained.

Example 9

By the same method as in Example 1, poly(N-propionylethyleneimine) having a number-average molecular weight of 1400 was obtained from 6.5 g (0.042 mol) of diethyl sulfate, 36.4 g (0.39 mol) of 2-ethyl-2-oxazoline, and 91 g of dehydrated ethyl acetate. Further, using 100 g of a side-chain primary aminopropyl-modified polydimethylsiloxane (weight-average molecular weight 70,000, amine equivalent 2500), an N-propionylethyleneimine-dimethylsiloxane copolymer was obtained as a light yellow rubber-like semisolid (140 g, yield 98%). The content percentage of an organopolysiloxane segment in the final product was 70% by mass, and the weight-average molecular weight was 100,000. Neutralization titration with hydrochloric acid using methanol as a solvent showed that no amino group remained.

Example 10

By the same method as in Example 1, poly(N-propionylethyleneimine) having a number-average molecular weight of 1300 was obtained from 6.5 g (0.042 mol) of diethyl sulfate, 34.4 g (0.36 mol) of 2-ethyl-2-oxazoline, and 87 g of dehydrated ethyl acetate. Further, using 100 g of a side-chain primary aminopropyl-modified polydimethylsiloxane (weight-average molecular weight, 32,000; amine equivalent, 2000), an N-propionylethyleneimine-dimethylsiloxane copolymer was obtained as a light yellow rubber-like semisolid (138 g, yield 98%). The content percentage of an organopolysiloxane segment in the final product was 71% by mass, and the weight-average molecular weight was 46,000. Neutralization titration with hydrochloric acid using methanol as a solvent showed that approx. 22% by mole of amino groups remained.

Example 11

By the same method as in Example 1, poly(N-propionylethyleneimine) having a number-average molecular weight of 900 was obtained from 6.5 g (0.042 mol) of diethyl sulfate, 20.1 g (0.21 mol) of 2-ethyl-2-oxazoline, and 57 g of dehydrated ethyl acetate. Further, using 100 g of a side-chain primary aminopropyl-modified polydimethylsiloxane (weight-average molecular weight, 36,000; amine equivalent, 2000), an N-propionylethyleneimine-dimethylsiloxane copolymer was obtained as a light yellow viscous semisolid (124 g, yield 98%). The content percentage of an organopolysiloxane segment in the final product was 79% by mass, and the weight-average molecular weight was 46,000. Neutralization titration with hydrochloric acid using methanol as a solvent showed that approx. 21% by mole of amino groups remained.

Example 12

By the same method as in Example 1, poly(N-propionylethyleneimine) having a number-average molecular weight of 1100 was obtained from 10.1 g (0.066 mol) of diethyl sulfate, 43.7 g (0.46 mol) of 2-ethyl-2-oxazoline, and 115 g of dehydrated ethyl acetate. Further, using 100 g of a side-chain primary aminopropyl-modified polydimethylsiloxane (weight-average molecular weight, 32,000; amine equivalent, 1600), an N-propionylethyleneimine-dimethylsiloxane copolymer was obtained as a light yellow rubber-like semisolid (148 g, yield 96%). The content percentage of an organopolysiloxane segment in the final product was 65% by mass, and the weight-average molecular weight was 49,000. Neutralization titration with hydrochloric acid using methanol as a solvent showed that no amino group remained.

Example 13

By the same method as in Example 1, poly(N-propionylethyleneimine) having a number-average molecular weight of 900 was obtained from 6.5 g (0.042 mol) of diethyl sulfate, 20.1 g (0.21 mol) of 2-ethyl-2-oxazoline, and 57 g of dehydrated ethyl acetate. Further, using 100 g of a side-chain primary aminopropyl-modified polydimethylsiloxane (weight-average molecular weight, 19,000, amine equivalent 2500), an N-propionylethyleneimine-dimethylsiloxane copolymer was obtained as a light yellow viscous semisolid (122 g, yield 96%). The content percentage of an organopolysiloxane segment in the final product was 79% by mass, and the weight-average molecular weight was 25,000. Neutralization titration with hydrochloric acid using methanol as a solvent showed that no amino group remained.

Example 14

By the same method as in Example 1, poly(N-propionylethyleneimine) having a number-average molecular weight of 1300 was obtained from 6.5 g (0.042 mol) of diethyl sulfate, 34.4 g (0.36 mol) of 2-ethyl-2-oxazoline, and 87 g of dehydrated ethyl acetate. Further, using 100 g of a side-chain primary aminopropyl-modified polydimethylsiloxane (weight-average molecular weight, 19,000; amine equivalent, 2500), an N-propionylethyleneimine-dimethylsiloxane copolymer was obtained as a light yellow viscous semisolid (135 g, yield 96%). The content percentage of an organopolysiloxane segment in the final product was 71% by mass, and the weight-average molecular weight was 27,000. Neutralization titration with hydrochloric acid using methanol as a solvent showed that no amino group remained.

Example 15

By the same method as in Example 1, poly(N-propionylethyleneimine) having a number-average molecular weight of 1300 was obtained from 6.5 g (0.042 mol) of diethyl sulfate, 34.4 g (0.36 mol) of 2-ethyl-2-oxazoline, and 87 g dehydrated ethyl acetate. Further, using 100 g of a side-chain primary aminopropyl-modified polydimethylsiloxane (weight-average molecular weight, 80,000; amine equivalent, 2500), an N-propionylethyleneimine-dimethylsiloxane copolymer was obtained as a light yellow rubber-like semisolid (135 g, yield 96%). The content percentage of an organopolysiloxane segment in the final product was 71% by mass, and the weight-average molecular weight was 113,000. Neutralization titration with hydrochloric acid using methanol as a solvent showed that no amino group remained.

Comparative Example 1

By the same method as in Example 1, poly(N-propionylethyleneimine) having a number-average molecular weight of 1600 was obtained from 8.7 g (0.056 mol) of diethyl sulfate, 55.3 g (0.59 mol) of 2-ethyl-2-oxazoline, and 136 g of dehydrated ethyl acetate. Further, using 100 g of a side-chain primary aminopropyl-modified polydimethylsiloxane (weight-average molecular weight, 90,000; amine equivalent, 1870), an N-propionylethyleneimine-dimethylsiloxane copolymer was obtained as a light yellow rubber-like solid (159 g, yield 97%). The content percentage of an organopolysiloxane segment in the final product was 61% by mass, and the weight-average molecular weight was 148,000. Neutralization titration with hydrochloric acid using methanol as a solvent showed that no amino group remained.

Comparative Example 2

By the same method as in Example 1, poly(N-propionylethyleneimine) having a number-average molecular weight of 1500 was obtained from 8.1 g (0.053 mol) of diethyl sulfate, 50.6 g (0.54 mol) of 2-ethyl-2-oxazoline, and 125 g of dehydrated ethyl acetate. Further, using 100 g of a side-chain primary aminopropyl-modified polydimethylsiloxane (weight-average molecular weight, 32,000; amine equivalent, 2000), an N-propionylethyleneimine-dimethylsiloxane copolymer was obtained as a light yellow rubber-like solid (154 g, yield 97%). The content percentage of an organopolysiloxane segment in the final product was 63% by mass, and the weight-average molecular weight was 51,000. Neutralization titration with hydrochloric acid using methanol as a solvent showed that no amino group remained.

Comparative Example 3

By the same method as in Example 1, poly(N-propionylethyleneimine) having a number-average molecular weight of 1300 was obtained from 6.5 g (0.042 mol) of diethyl sulfate, 34.4 g (0.36 mol) of 2-ethyl-2-oxazoline, and 87 g of dehydrated ethyl acetate. Further, using 100 g of a side-chain primary aminopropyl-modified polydimethylsiloxane (weight-average molecular weight, 8000; amine equivalent, 2500), an N-propionylethyleneimine-dimethylsiloxane copolymer was obtained as a light yellow viscous semisolid (137 g, yield 97%). The content percentage of an organopolysiloxane segment in the final product was 71% by mass, and the weight-average molecular weight of organopolysiloxane was 11,000. Neutralization titration with hydrochloric acid using methanol as a solvent showed that no amino group remained.

Comparative Example 4

By the same method as in Example 1, poly(N-propionylethyleneimine) having a number-average molecular weight of 1300 was obtained from 6.5 g (0.042 mol) of diethyl sulfate, 34.4 g (0.36 mol) of 2-ethyl-2-oxazoline, and 87 g of dehydrated ethyl acetate. Further, using 100 g of a side-chain primary aminopropyl-modified polydimethylsiloxane (weight-average molecular weight 110,000, amine equivalent 2500), an N-propionylethyleneimine-dimethylsiloxane copolymer was obtained as a light yellow rubber-like solid (135 g, yield 96%). The content percentage of an organopolysiloxane segment in the final product was 71% by mass, and the weight-average molecular weight of organopolysiloxane was 155,000. Neutralization titration with hydrochloric acid using methanol as a solvent showed that no amino group remained.

Comparative Example 5

By the same method as in Example 1, poly(N-propionylethyleneimine) having a number-average molecular weight of 500 was obtained from 8.1 g (0.053 mol) of diethyl sulfate, 12.4 g (0.13 mol) of 2-ethyl-2-oxazoline, and 44 g of dehydrated ethyl acetate. Further, using 100 g of a side-chain primary aminopropyl-modified polydimethylsiloxane (weight-average molecular weight, 40,000; amine equivalent, 2000), an N-propionylethyleneimine-dimethylsiloxane copolymer was obtained as a light yellow rubber-like solid (116 g, yield 96%). This product was a solid insoluble in various solvents.

Comparative Example 6

By the same method as in Example 1, poly(N-propionylethyleneimine) having a number-average molecular weight of 5800 was obtained from 1.5 g (0.010 mol) of diethyl sulfate, 39.4 g (0.42 mol) of 2-ethyl-2-oxazoline, and 87 g of dehydrated ethyl acetate. Further, using 100 g of a side-chain primary aminopropyl-modified polydimethylsiloxane (weight-average molecular weight, 26,000; amine equivalent, 11,000), an N-propionylethyleneimine-dimethylsiloxane copolymer was obtained as a light yellow rubber-like solid (135 g, yield 96%). The content percentage of an organopolysiloxane segment in the final product was 71% by mass, and the average molecular weight was 37,000. Neutralization titration with hydrochloric acid using methanol as a solvent showed that no amino group remained.

Comparative Example 7

By the same method as in Example 1, poly(N-propionylethyleneimine) having a number-average molecular weight of 1900 was obtained from 4.5 g (0.029 mol) of diethyl sulfate, 36.3 g (0.39 mol) of 2-ethyl-2-oxazoline, and 87 g of dehydrated ethyl acetate. Further, using 100 g of a side-chain primary aminopropyl-modified polydimethylsiloxane (weight-average molecular weight 35,000; amine equivalent, 3600), an N-propionylethyleneimine-dimethylsiloxane copolymer was obtained as a light yellow rubber-like solid (135 g, yield 96%). The content percentage of an organopolysiloxane segment in the final product was 71% by mass, and the weight-average molecular weight was 49,000. Neutralization titration with hydrochloric acid using methanol as a solvent showed that no amino group remained.

Comparative Example 8

By the same method as in Example 1, poly(N-propionylethyleneimine) having a number-average molecular weight of 700 was obtained from 8.1 g (0.053 mol) of diethyl sulfate, 18.5 g (0.20 mol) of 2-ethyl-2-oxazoline, and 57 g of dehydrated ethyl acetate. Further, using 100 g of a side-chain primary aminopropyl-modified polydimethylsiloxane (weight-average molecular weight, 80,000; amine equivalent, 2000), an N-propionylethyleneimine-dimethylsiloxane copolymer was obtained as a light yellow rubber-like solid (120 g, yield 95%). This product was a solid insoluble in various solvents.

Comparative Example 9

By the same method as in Example 1, poly(N-propionylethyleneimine) having a number-average molecular weight of 5200 was obtained from 3.2 g (0.021 mol) of diethyl sulfate, 92.8 g (0.98 mol) of 2-ethyl-2-oxazoline, and 205 g of dehydrated ethyl acetate. Further, using 100 g of a side-chain primary aminopropyl-modified polydimethylsiloxane (weight-average molecular weight, 50,000; amine equivalent, 3800), N-propionylethyleneimine-dimethylsiloxane copolymer was obtained as a light yellow rubber-like solid (188 g, yield 96%). The content percentage of an organopolysiloxane segment in the final product was 51% by mass, and the weight-average molecular weight was 98,000. Neutralization titration with hydrochloric acid using methanol as a solvent showed that approx. 24% by mole of amino groups remained.

Comparative Example 10

By the same method as in Example 1, poly(N-propionylethyleneimine) having a number-average molecular weight 2700 was obtained from 0.8 g (0.005 mol) of diethyl sulfate, 12.8 g (0.14 mol) of 2-ethyl-2-oxazoline, and 29 g of dehydrated ethyl acetate. Further, using 100 g of a side-chain primary aminopropyl-modified polydimethylsiloxane (weight-average molecular weight 100,000, amine equivalent 20,000), an N-propionylethyleneimine-dimethylsiloxane copolymer was obtained as a light yellow rubber-like solid (111 g, yield 98%). The content percentage of an organopolysiloxane segment in the final product was 88% by mass, and the weight-average molecular weight was 114,000. Neutralization titration with hydrochloric acid using methanol as a solvent showed that no amino group remained.

Comparative Example 11

By the same method as in Example 1, poly(N-propionylethyleneimine) having a number-average molecular weight of 1200 was obtained from 0.6 g (0.004 mol) of diethyl sulfate, 3.6 g (0.04 mol) of 2-ethyl-2-oxazoline, and 9 g of dehydrated ethyl acetate. Further, using 100 g of a side-chain primary aminopropyl-modified polydimethylsiloxane (weight-average molecular weight 100,000, amine equivalent 20,000), an N-propionylethyleneimine-dimethylsiloxane copolymer was obtained as a light yellow rubber-like solid (95 g, yield 95%). The content percentage of an organopolysiloxane segment in the final product was 96% by mass, and the weight-average molecular weight was 104,000. Neutralization titration with hydrochloric acid using methanol as a solvent showed that approx. 30% by mole of amino groups remained.

Physical properties of the organopolysiloxanes obtained in Examples 1 to 15 are shown in Table 1. Physical properties of the organopolysiloxanes obtained in Comparative Examples 1 to 11 are shown in Table 2.

TABLE 1

| | Examples | | | | | | | |
|---|---|---|---|---|---|---|---|---|
| | 1 | 2 | 3 | 4 | 5 | 6 | 7 | 8 |
| a/b | 65/35 | 68/32 | 70/30 | 71/29 | 79/21 | 68/32 | 82/18 | 75/25 |
| MWsi | 32000 | 32000 | 20000 | 40000 | 35000 | 32000 | 65000 | 37000 |
| MWox | 1400 | 1100 | 1400 | 1300 | 900 | 1200 | 1000 | 1500 |
| MWg | 2000 | 1750 | 2500 | 2500 | 2600 | 2000 | 3500 | 3500 |
| MWt | 49000 | 47000 | 29000 | 56000 | 51000 | 46000 | 79000 | 49000 |

| | Examples | | | | | |
|---|---|---|---|---|---|---|
| | 9 | 10 | 11 | 12 | 13 | 14 | 15 |
| a/b | 70/30 | 71/29 | 79/21 | 65/35 | 79/21 | 71/29 | 71/29 |
| MWsi | 70000 | 32000 | 36000 | 32000 | 19000 | 19000 | 80000 |
| MWox | 1400 | 1300 | 900 | 1100 | 900 | 1300 | 1300 |
| MWg | 2500 | 2500 | 2500 | 1600 | 2500 | 2500 | 2500 |
| MWt | 100000 | 46000 | 46000 | 49000 | 25000 | 27000 | 113000 |

TABLE 2

| | Comparative Examples | | | | | | | | | | |
|---|---|---|---|---|---|---|---|---|---|---|---|
| | 1 | 2 | 3 | 4 | 5 | 6 | 7 | 8 | 9 | 10 | 11 |
| a/b | 61/39 | 63/37 | 71/29 | 71/29 | — | 71/29 | 71/29 | — | 51/49 | 88/12 | 96/4 |
| MWsi | 90000 | 32000 | 8000 | 110000 | 40000 | 26000 | 35000 | 80000 | 50000 | 100000 | 100000 |
| MWox | 1600 | 1500 | 1300 | 1300 | 500 | 5800 | 1900 | 700 | 5200 | 2700 | 1200 |
| MWg | 1870 | 2000 | 2500 | 2500 | — | 11000 | 3600 | — | 5000 | 20000 | 28600 |
| MWt | 148000 | 51000 | 11000 | 155000 | — | 37000 | 49000 | — | 98000 | 114000 | 104000 | a/b: Mass ratio of an organopolysiloxane segment (a) and a poly(N-acylalkyleneimine) segment (b)
MWsi: Weight-average molecular weight of an organopolysiloxane segment as a main chain
MWox: Number-average molecular weight of a poly(N-acylalkyleneimine) segment
MWg: Weight-average molecular weight of an organopolysiloxane segment between adjacent poly(N-acylalkyleneimine) segments
MWt: Weight-average molecular weight of an organopolysiloxane Evaluation Test The organopolysiloxanes obtained in Examples 1 to 15 and Comparative Examples 1 to 11 were evaluated for the following properties. The results of Examples 1 to 15 are shown in Table 4. The results of Comparative Examples 1 to 11 are shown in Table 5.

(1) Extensibility

A solution of 10% by mass organopolysiloxane in ethanol was prepared, and ethanol was spontaneously evaporated to prepare a polymer membrane having a length of 20 mm, a width of 5 mm, and a thickness of 1.0 mm.

This membrane was extended 300% in the longitudinal direction at an extension speed of 50 mm/min at a temperature of 20° C. and a relative humidity of 65% using a tensile tester (Tensilon Tensile Tester, Model RTC-1210A, Orientech Co., Ltd.). Membranes that did not break after being left at an extension rate of 300% for 3 minutes were rated as B, and those that broke were rated as D.

(2) Curl Maintaining Ability

A bundle of untreated straight Japanese hair having a length 25 cm (L0) and a mass of 4 g was washed with a model shampoo having the composition shown in Table 3 (the model shampoo mentioned below had the same composition) and dried with a towel.

Subsequently, 0.4 g of a solution of organopolysiloxane in ethanol having a concentration of 5% by mass was made into a mist and applied uniformly to the above-mentioned hair bundle, and the bundle was wound on a glass cylinder having a diameter of 2 cm. The bundle was air-dried over 8 hours at a temperature of 20° C. and a relative humidity of 60%, removed from the cylinder, and hung with one end thereof fixed, and the length (L1) was measured. Then, a fine styling comb (New Delrin Comb, Uehara Cell) was carefully passed through the hair bundle 10 times, and hung with one end thereof fixed, and the length (L2) was measured.

The curl maintaining rate (%) was obtained by the following formula (IV) from the measured values. Evaluation was made by rating 82% or higher as A, lower than 82% and 77% or higher as B, lower than 77% and 750 or higher as C, and lower than 75% as D.

$$[(L0-L2)/(L0-L1)] \times 100 \quad (IV)$$

TABLE 3

| Composition of model shampoo | |
|---|---|
| Model shampoo | Mixture amount (% by mass) |
| 25% aqueous solution of polyoxyethylene (2.5 E.O) sodium lauryl ether sulfate | 62.00 |
| Lauric diethanolamide | 2.28 |
| Disodium edetate | 0.10 |
| Sodium benzoate | 0.50 |
| Oxybenzone | 0.03 |
| Phosphoric acid (75% aqueous solution) | 0.10 |
| Dibutylated hydroxytoluene | 0.01 |
| Sodium chloride | 0.80 |
| Red No. 106 | 0.00012 |

TABLE 3-continued

| Composition of model shampoo | |
|---|---|
| Model shampoo | Mixture amount (% by mass) |
| Perfume | 0.26 |
| Purified water | Balance |

(3) Softness of Hair

A bundle of permed Japanese hair having a length of 20 cm and a weight of 4 g was washed with the model shampoo and dried with a towel.

Subsequently, 0.4 g of a solution of organopolysiloxane in ethanol having a concentration of 5% by mass was made into a mist, applied uniformly to the above-mentioned hair bundle, and air-dried over 4 hours, and sensory evaluation was made by a panel of five experts. Evaluation was made by rating "Feels soft" as 5 points, "Feels slightly soft" as 4 points, "Undecided" as 3 points, "Feels not very soft" as 2 points, and "Does not feel soft" as 1 point. A was given with the total score of the five experts being 22 points or higher, B with lower than 22 points and 17 points or higher, C with lower than 17 points and 11 points or higher, and D with lower than 11 points.

(4) Wash Property

A bundle of dried permed Japanese hair having a length of 25 cm and a weight of 4 g was prepared, and 0.4 g of a solution of organopolysiloxane in ethanol having a concentration of 5% by mass was made into a mist, applied uniformly to the above-mentioned hair bundle, and dried with a dryer. Then, 1 g of the model shampoo was applied, rinsed with tap water at 40° C., and dried with a dryer.

This procedure was repeated 14 times, and the feel to the touch was compared with that of a hair bundle untreated with a polymer as a control hair bundle to evaluate the degree of residual organopolysiloxanes. Sensory evaluation was made by a panel of five experts. Evaluation was made by rating "No difference" as 5 points, "Not much difference" as 4 points, "Undecided" as 3 points, "Slight difference" as 2 points, "Different" as 1 point, as compared with the control hair bundle. A was given with the total score of the five experts being 22 points or higher, B with lower than 22 points and 17 points or higher, C with lower than 17 points and 11 points or higher, and D with lower than 11 points.

(5) Ethanol Solubility

Evaluation was made by rating an organopolysiloxane that could be dissolved in ethanol at 40% by mass or more or uniformly dispersed as B and others as D.

(6) Water Dispersibility

Evaluation was made by rating an organopolysiloxane that could be dissolved in purified water at 30% by mass or more or uniformly dispersed as B, and others were rated as D.

TABLE 4

| | Examples | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| Extensibility | B | B | B | B | B | B | B | B | B | B | B | B | B | B | B |
| Curl maintaining ability | A | B | B | A | B | A | B | B | A | A | B | A | C | B | A |
| Softness of hair | C | A | A | A | A | B | A | B | B | A | A | B | A | A | B |
| Wash property | A | B | B | B | B | B | C | A | B | A | B | B | B | B | B |
| Ethanol solvability | B | B | B | B | B | B | B | B | B | B | B | B | B | B | B |
| Water dispersibility | B | B | B | B | B | B | B | B | B | B | B | B | B | B | B |

TABLE 5

|  | Comparative Examples | | | | | | | | | | |
| --- | --- | --- | --- | --- | --- | --- | --- | --- | --- | --- | --- |
|  | 1 | 2 | 3 | 4 | 5 | 6 | 7 | 8 | 9 | 10 | 11 |
| Extensibility | D | D | D | B | — | D | D | — | D | D | D |
| Curl maintaining ability | D | D | D | C | — | D | C | — | D | C | D |
| Softness of hair | C | C | C | C | — | D | D | — | D | C | C |
| Wash property | C | C | C | D | — | C | C | — | B | B | B |
| Ethanol solvability | B | B | B | B | D | B | B | D | B | B | D |
| Water dispersibility | B | B | B | D | D | B | B | D | B | B | D |

—: Immeasurable

Examples 16 to 20 and Comparative Examples 12 and 13

Hair cosmetics having compositions shown in Table 6 were prepared and evaluated for "setting performance," "set holding performance," and "softness of hair after setting" according to the following methods and criteria. The evaluation results are also shown in Table 6. In the table, the mixture amount of each component is expressed with % by mass.

Evaluation Methods

1) Evaluation of "Setting Performance"

The head hair of five experts of a panel with permed hair of a medium length (length of hair reaching the shoulder or so) was washed with the model shampoo and dried with a dryer, and a hairdresser applied a styling wax as required and set the hair.

Then, sensory evaluation of the setting performance was made by each expert. Evaluation was made by rating "Feel good setting performance" as 5 points, "Feel slightly good setting performance" as 4 points, "Undecided" as 3 points, "Feel not very good setting performance" as 2 points, and "Feel not good setting performance" as 1 point. A was given with the total score of the five experts being 22 points or higher, B with lower than 22 points and 17 points or higher, C with lower than 17 points and 11 points or higher, and D with lower than 11 points.

2) Evaluation of "Set Holding Performance"

The head hair of five experts of a panel with permed hair of a medium length (length of hair reaching the shoulder or so) was washed with a model shampoo and dried with a dryer, and a hairdresser applied a styling wax as required and set the hair.

Then, the experts were instructed to have normal activity for 4 hours, and sensory evaluation was made by each panelist regarding the set holding performance. Evaluation was made by rating "Feel good set hold" as 5 points, "Feel slightly good set hold" as 4 points, "Undecided" as 3 points, "Feel not very good set hold" as 2 points, and "Feel no good set hold" as 1 point. A was given with the total score of the five experts being 22 points or higher, B with lower than 22 points and 17 points or higher, C with lower than 17 points and 11 points or higher, and D with lower than 11 points.

3) Evaluation of "Softness of Hair after Setting"

The head hair of five experts of a panel with permed hair of a medium length (length of hair reaching the shoulder or so) was washed with the model shampoo and dried with a dryer, and a hairdresser applied a styling wax as required and set the hair.

Then, sensory evaluation was made by each panelist regarding softness of hair after setting. Evaluation was made by rating "Hair feels soft" as 5 points, "hair feels slightly soft" as 4 points, "Undecided" as 3 points, "Hair feels not very soft" as 2 points, and "Hair feels not soft" as 1 point. A was given with the total score of the five experts being 22 points or higher, B with lower than 22 points and 17 points or higher, C with lower than 17 points and 11 points or higher, and D with lower than 11 points.

TABLE 6

|  | Examples | | | | | Comparative Examples | |
| --- | --- | --- | --- | --- | --- | --- | --- |
|  | 16 | 17 | 18 | 19 | 20 | 12 | 13 |
| Organopolysiloxane A*[1] | 2.5 | — | 1.5 | — | 2.0 | — | — |
| Organopolysiloxane B*[2] | — | 2.5 | — | 1.5 | 1.5 | — | — |
| Organopolysiloxane C*[3] | — | — | — | — | — | 2.5 | — |
| Acrylic acid-alkyl methacrylate copolymer*[4] | — | — | 0.5 | 0.5 | 0.5 | 0.5 | 1.0 |
| Dimethyl polysiloxane*[5] | 5.0 | 5.0 | 5.0 | 5.0 | 5.0 | 5.0 | 5.0 |
| Polyoxyethylene isocetyl ether (20 E.O.) | 1.5 | 1.5 | 1.5 | 1.5 | 1.5 | 1.5 | 1.5 |
| Polyoxyethylene lauryl ether (23 E.O.) | 1.5 | 1.5 | 1.5 | 1.5 | 1.5 | 1.5 | 1.5 |
| Isopropyl palmitate | 3.0 | 3.0 | 3.0 | 3.0 | 3.0 | 3.0 | 3.0 |
| Vaseline | 1.0 | 1.0 | 1.0 | 1.0 | 1.0 | 1.0 | 1.0 |
| Ethanol | 6.0 | 6.0 | 5.0 | 5.0 | 6.0 | 6.0 | 5.0 |
| Disodium edetate | 0.1 | 0.1 | 0.1 | 0.1 | 0.1 | 0.1 | 0.1 |
| Glycerine | 5.0 | 5.0 | 5.0 | 5.0 | 5.0 | 5.0 | 5.0 |
| Sodium hydroxide | As required | As required | As required | As required | As required | As required | As required |
| Methyl paraoxybenzoate | 0.3 | 0.3 | 0.3 | 0.3 | 0.3 | 0.3 | 0.3 |
| Perfume | 0.1 | 0.1 | 0.1 | 0.1 | 0.1 | 0.1 | 0.1 |
| Water | Balance | Balance | Balance | Balance | Balance | Balance | Balance |
| Setting performance | B | A | C | B | A | C | C |
| Set holding performance after setting | A | B | B | C | A | D | D |
| Softness of hair after setting | B | B | A | A | B | A | C |

*[1]Organopolysiloxane obtained in Example 10
*[2]Organopolysiloxane obtained in Example 11
*[3]Organopolysiloxane obtained in Comparative Example 6
*[4]Carbopol ETD-2020 (Noveon, Inc.)
*[5]Silicone SH200C FLUID 5000CS (Dow Corning Toray Co., Ltd.)

Examples 21 to 23 and Comparative Example 14

Hair cosmetics having compositions shown in Table 7 (emulsified cream type, soft) were prepared and evaluated for "setting performance" and "set holding performance" according to the above-mentioned methods and criteria and for "smoothness of hair after setting" according to the following method and criteria. The evaluation results are also shown in Table 7. In the table, the mixture amount of each component is expressed with % by mass.

Evaluation of "Smoothness of Hair after Setting"

Evaluation Method

The head hair of five experts of a panel with permed hair of a medium length (length of hair reaching the shoulder or so) was washed with the model shampoo and dried with a dryer, and a hairdresser applied a styling wax as required and set the hair.

Then, sensory evaluation was made by each panelist regarding smoothness of the hair after setting. Evaluation was made by rating "Hair feels smooth" as 5 points, "Hair feels slightly smooth" as 4 points, "Undecided" as 3 points, "Hair feels not very smooth" as 2 points, and "Hair feels not smooth" as 1 point. A was given with the total score of the five experts being 22 points or higher, B with lower than 22 points and 17 points or higher, C with lower than 17 points and 11 points or higher, and D with lower than 11 points.

TABLE 7

|  | Examples | | | Comparative Example |
|---|---|---|---|---|
|  | 21 | 22 | 23 | 14 |
| Organopolysiloxane A*1 | 0.5 | — | 0.3 | — |
| Organopolysiloxane B*2 | — | 0.5 | 0.2 | — |
| Liquid paraffin | 3.0 | 3.0 | 3.0 | 5.0 |
| Dimethyl polysiloxane*5 | 3.0 | 3.0 | 3.0 | 3.0 |
| Polyoxyethylene sorbitan monostearate (20 EO) | 2.0 | 2.0 | 2.0 | 2.0 |
| Lipophilic glyceryl monostearate*6 | 3.0 | 3.0 | 3.0 | 5.0 |
| Behenyl alcohol | 8.0 | 8.0 | 8.0 | 8.0 |
| Paraffin | 5.0 | 5.0 | 5.0 | 5.0 |
| Disodium edetate | 0.1 | 0.1 | 0.1 | 0.1 |
| 1,3-Butylene glycol | 5.0 | 5.0 | 5.0 | 5.0 |
| Phenoxyethanol | 0.3 | 0.3 | 0.3 | 0.3 |
| Ethanol | 0.5 | 0.5 | 0.5 | 0.5 |
| Perfume | 0.1 | 0.1 | 0.1 | 0.1 |
| Water | Balance | Balance | Balance | Balance |
| Setting performance | B | A | A | C |
| Set holding performance after setting | A | B | A | C |
| Smoothness of hair after setting | B | B | B | D |

*1Organopolysiloxane obtained in Example 10
*2Organopolysiloxane obtained in Example 11
*5Silicone SH200C FLUID 5000CS (Dow Corning Toray Co., Ltd.)
*6RHEODOL MS-60 (Kao Corporation)

Examples 24 to 26 and Comparative Examples 15 and 16

Hair cosmetics having the compositions shown in Table 8 (emulsified cream type, hard) were prepared, and "setting performance" and "set holding performance" were evaluated according to the above-mentioned method and criteria. Further, "no greasiness of hair after setting" was evaluated according to the following method and criteria. The evaluation results combined are also shown in Table 8. The mixture amount of each component in the table is expressed with % by mass.

Evaluation of "No Greasiness of Hair after Setting"

Evaluation Method

The head hair of five experts of a panel with permed hair of a medium length (length of hair reaching the shoulder or so) was washed with the model shampoo and dried with a dryer, and a hairdresser applied a styling wax as required and set the hair.

Then, sensory evaluation was made by each expert panelist regarding greasiness of hair after setting. Evaluation was made by rating "Feels not greasy" as 5 points, "Feel not very greasy" as 4 points, "Undecided" as 3 points, "Feels slightly greasy" as 2 points, and "Feels greasy" as 1 point. A was given with the total score of the five experts being 22 points or higher, B with lower than 22 points and 17 points or higher, C with lower than 17 points and 11 points or higher, and D with lower than 11 points.

TABLE 8

|  | Examples | | | Comparative Examples | |
|---|---|---|---|---|---|
|  | 24 | 25 | 26 | 15 | 16 |
| Organopolysiloxane A*1 | 1.5 | — | 0.7 | — | — |
| Organopolysiloxane B*2 | — | 1.5 | 0.7 | — | — |
| Organopolysiloxane C*3 | — | — | — | 1.5 | — |
| Liquid paraffin | 3.0 | 3.0 | 3.0 | 3.0 | 3.0 |
| Microcrystalline wax | 5.0 | 5.0 | 5.0 | 5.0 | 5.0 |
| Polyoxyethylene sorbitan monostearate (20 EO) | 2.0 | 2.0 | 2.0 | 2.0 | 2.0 |
| Lipophilic glyceryl monostearate*6 | 5.0 | 5.0 | 5.0 | 5.0 | 5.0 |
| Cetanol | 8.0 | 8.0 | 8.0 | 8.0 | 8.0 |
| Vaseline | 1.5 | 1.5 | 1.5 | 1.5 | 3.0 |
| Beeswax | 1.5 | 1.5 | 1.5 | 1.5 | 3.0 |
| Disodium edetate | 0.1 | 0.1 | 0.1 | 0.1 | 0.1 |
| 1,3-Butylene glycol | 5.0 | 5.0 | 5.0 | 5.0 | 5.0 |
| Phenoxyethanol | 0.3 | 0.3 | 0.3 | 0.3 | 0.3 |
| Ethanol | 1.8 | 1.8 | 1.8 | 1.8 | 1.8 |
| Perfume | 0.1 | 0.1 | 0.1 | 0.1 | 0.1 |
| Water | Balance | Balance | Balance | Balance | Balance |
| Setting performance | A | A | A | D | C |
| Holding performance after setting | A | B | A | C | C |
| No greasiness of hair after setting | B | A | A | C | D |

*1Organopolysiloxane obtained in Example 10
*2Organopolysiloxane obtained in Example 11
*3Organopolysiloxane obtained in Comparative Example 6
*6RHEODOL MS-60 (Kao Corporation)

Examples 31 to 56 and Reference Examples 31 to 54

Hair cosmetics having the compositions shown in Tables 9 to 12 were prepared by a usual method. The hair cosmetics having the compositions shown in Tables 9 and 11 were aerosol-type foamy hair cosmetics. The hair cosmetics having the compositions shown in Tables 10 and 12 were non-aerosol-type mists. pH is the value when the composition was diluted 20-fold by mass with water at 25° C. The mixture ratio of each component in Tables 9 to 12 is expressed with % by mass.

TABLE 9

| | Examples | | | | | | | | |
|---|---|---|---|---|---|---|---|---|---|
| | 31 | 32 | 33 | 34 | 35 | 36 | 37 | 38 | 39 |
| Aqueous malic acid (50% by mass aqueous solution) | 3.5 | | | | 3.5 | | | | 1.0 |
| Lactic acid (90% by mass aqueous solution) | | 2.0 | | | | 2.0 | | | 1.5 |
| Glycolic acid (70% by mass aqueous solution) | | | 2.5 | | | | 2.5 | | |
| Citric acid (50% by mass aqueous solution) | | | | 3.5 | | | | 3.5 | |
| Benzyl alcohol | 1.0 | 1.0 | 1.0 | 1.0 | 0.2 | 0.2 | 0.2 | 0.2 | |
| Dipropylene glycol | | | | | 0.8 | 0.8 | 0.8 | 0.8 | |
| 1,3-Butylene glycol | | | | | | | | | 0.2 |
| Phenoxyethanol | | | | | | | | | |
| Benzyloxyethanol | | | | | | | | | 1.0 |
| Organopolysiloxane A*1 | 2.5 | 2.5 | 2.5 | 2.5 | 1.0 | | 1.0 | | 1.5 |
| Organopolysiloxane B*2 | | | | | 0.2 | 1.5 | 0.2 | 1.5 | 0.1 |
| Organopolysiloxane D*7 | | | | | | | | | 0.5 |
| Organopolysiloxane E*8 | | | | | | | | | |
| Vinylpyrrolidone-N,N-dimethylaminoethyl methacrylic acid copolymer diethyl sulfate | 0.5 | 0.5 | 0.5 | 0.5 | 0.5 | 0.5 | 0.5 | 0.5 | 0.5 |
| Stearyl trimethyl ammonium chloride (30% by mass aqueous solution) | 1.5 | 1.5 | 1.5 | 1.5 | 1.5 | 1.5 | 1.5 | 1.5 | 1.5 |
| Polyoxyethylene tridecyl ether*9 | 0.5 | 0.5 | 0.5 | 0.5 | 0.5 | 0.5 | 0.5 | 0.5 | 0.5 |
| Polyoxyethylene-polyoxypropylene stearyl ether*10 | 2.0 | 2.0 | 2.0 | 2.0 | 2.0 | 2.0 | 2.0 | 2.0 | 2.0 |
| Polyoxyethylene cetyl ether*11 | 0.5 | 0.5 | 0.5 | 0.5 | 0.5 | 0.5 | 0.5 | 0.5 | 0.5 |
| Polyoxyethylene-methyl polysiloxane copolymer*12 | | | | | | | | | |
| 95% synthetic ethylalcohol | 12.0 | 12.0 | 12.0 | 12.0 | 12.0 | 12.0 | 12.0 | 12.0 | 12.0 |
| Neopentyl glycol dicaprate | | | | | | | | | |
| Isopropyl palmitate | | | | | | | | | |
| Purified water | Balance | Balance | Balance | Balance | Balance | Balance | Balance | Balance | Balance |
| Sodium hydroxide | As required | As required | As required | As required | As required | As required | As required | As required | As required |
| Perfume | 0.1 | 0.1 | 0.1 | 0.1 | 0.1 | 0.1 | 0.1 | 0.1 | 0.1 |
| Propellant (LPG, 4.4 Pa) | 7.0 | 7.0 | 7.0 | 7.0 | 7.0 | 7.0 | 7.0 | 7.0 | 7.0 |
| pH | 3.7 | 3.7 | 3.7 | 3.7 | 3.7 | 3.7 | 3.7 | 3.7 | 3.7 |

| | Examples | | | | | | |
|---|---|---|---|---|---|---|---|
| | 40 | 41 | 42 | 43 | 44 | 45 | 46 |
| Aqueous malic acid (50% by mass aqueous solution) | | | 0.5 | 0.5 | 0.3 | 0.2 | 0.2 |
| Lactic acid (90% by mass aqueous solution) | 1.5 | 1.5 | 1.0 | 2.5 | 2.1 | 1.5 | 1.5 |
| Glycolic acid (70% by mass aqueous solution) | | 1.5 | | | | | 0.2 |
| Citric acid (50% by mass aqueous solution) | 1.0 | | 2.0 | | | | 0.2 |
| Benzyl alcohol | | | | 0.2 | 0.2 | 0.1 | 0.2 |
| Dipropylene glycol | | 1.5 | 1.5 | 0.3 | 0.5 | 0.3 | |
| 1,3-Butylene glycol | 0.2 | | | 0.7 | 0.5 | 0.5 | 0.5 |
| Phenoxyethanol | | 0.1 | 0.1 | | | | |
| Benzyloxyethanol | 1.0 | | | | | | 0.2 |
| Organopolysiloxane A*1 | 1.5 | 1.5 | 1.5 | 1.5 | 1.2 | 2.5 | 3.0 |
| Organopolysiloxane B*2 | 0.1 | 0.1 | 0.1 | | 0.1 | 0.1 | 0.1 |
| Organopolysiloxane D*7 | 0.5 | 0.5 | 0.5 | 0.5 | 0.2 | 0.1 | 0.1 |
| Organopolysiloxane E*8 | | | 0.2 | | | | |
| Vinylpyrrolidone-N,N-dimethylaminoethyl methacrylic acid copolymer diethyl sulfate | 0.5 | 0.5 | 0.5 | 0.4 | 1.0 | 1.2 | 1.2 |
| Stearyl trimethyl ammonium chloride (30% by mass aqueous solution) | 1.5 | 1.5 | 1.5 | 1.5 | 1.5 | 1.5 | 1.5 |
| Polyoxyethylene tridecyl ether*9 | 0.5 | 0.5 | 0.5 | 0.5 | 0.5 | 0.5 | 0.5 |
| Polyoxyethylene-polyoxypropylene stearyl ether*10 | 2.0 | 2.0 | 2.0 | 2.0 | | | 2.0 |
| Polyoxyethylene cetyl ether*11 | 0.5 | 0.5 | 0.5 | 0.5 | 0.5 | 0.5 | 0.5 |
| Polyoxyethylene-methyl polysiloxane copolymer*12 | | | | 0.3 | | | 0.5 |
| 95% synthetic ethylalcohol | 12.0 | 12.0 | 12.0 | 12.0 | 12.0 | 12.0 | 12.0 |
| Neopentyl glycol dicaprate | | | | 2.0 | | | 1.0 |
| Isopropyl palmitate | | | | 0.5 | | | 0.5 |
| Purified water | Balance | Balance | Balance | Balance | Balance | Balance | Balance |
| Sodium hydroxide | As required | As required | As required | As required | As required | As required | As required |

TABLE 9-continued

|  |  |  |  |  |  |  |  |
|---|---|---|---|---|---|---|---|
| Perfume | 0.1 | 0.1 | 0.1 | 0.1 | 0.1 | 0.1 | 0.1 |
| Propellant (LPG, 4.4 Pa) | 7.0 | 7.0 | 7.0 | 7.0 | 7.0 | 7.0 | 7.0 |
| pH | 3.7 | 3.7 | 3.7 | 3.7 | 3.7 | 3.7 | 3.7 |

TABLE 10

|  | Examples |  |  |  |  |  |  |  |  |  |
|---|---|---|---|---|---|---|---|---|---|---|
|  | 47 | 48 | 49 | 50 | 51 | 52 | 53 | 54 | 55 | 56 |
| Aqueous malic acid (50% by mass aqueous solution) | 2.5 | 2.5 | 2.5 | 2.5 | 2.5 | 2.5 | 2.5 | 2.5 | 1.8 | 1.8 |
| Lactic acid (90% by mass aqueous solution) | 1.4 | 1.4 | 1.4 | 1.4 | 1.4 | 1.4 | 1.4 | 1.4 | 1.0 | 1.0 |
| Glycolic acid (70% by mass aqueous solution) |  |  |  |  |  |  |  |  |  |  |
| Citric acid (50% by mass aqueous solution) |  |  |  |  |  |  |  |  |  |  |
| Benzyl alcohol | 0.2 | 0.2 | 0.2 | 0.2 | 0.2 | 0.2 | 0.2 | 0.2 | 0.2 | 0.2 |
| Dipropylene glycol | 1.0 | 1.0 | 1.0 | 1.0 | 1.0 | 1.0 | 1.0 | 1.0 | 1.0 | 1.0 |
| 1,3-Butylene glycol |  |  |  |  |  |  |  |  |  |  |
| Phenoxyethanol |  |  |  |  |  |  |  |  |  |  |
| Benzyloxyethanol |  |  |  |  |  |  |  |  |  |  |
| Organopolysiloxane A[*1] | 0.4 | 1.9 | 0.5 | 2.0 | 0.5 | 2.0 | 1.0 | 4.0 | 0.5 | 2.0 |
| Organopolysiloxane B[*2] |  | 0.1 | 0.1 | 0.1 | 0.1 | 0.1 | 0.1 | 0.1 | 0.1 | 0.1 |
| Organopolysiloxane D[*7] | 1.5 | 1.3 | 0.5 | 0.5 | 3.0 | 3.0 | 1.5 | 1.5 | 1.5 | 1.5 |
| Organopolysiloxane E[*8] |  |  |  |  |  |  |  |  |  |  |
| Vinylpyrrolidone-N,N-dimethylaminoethyl methacrylic acid copolymer diethyl sulfate | 0.2 | 1.0 | 0.2 | 1.0 | 0.2 | 1.0 | 0.2 | 1.0 | 0.2 | 1.0 |
| Stearyl trimethyl ammonium chloride (30% by mass aqueous solution) | 0.8 | 0.8 | 0.8 | 0.8 | 0.8 | 0.8 | 0.8 | 0.8 | 0.8 | 0.8 |
| Polyoxyethylene tridecyl ether[*9] | 0.2 | 0.4 | 0.2 | 0.4 | 0.2 | 0.4 | 0.2 | 0.4 | 0.2 | 0.4 |
| Polyoxyethylene-polyoxypropylene stearyl ether[*10] |  |  |  |  |  |  |  |  |  |  |
| Polyoxyethylene cetyl ether[*11] |  |  |  |  |  |  |  |  |  |  |
| Polyoxyethylene-methyl polysiloxane copolymer[*12] |  | 0.6 |  | 0.6 |  | 0.6 |  | 0.6 |  | 0.6 |
| Aminoethylaminopropylsiloxane-dimethylsiloxane copolymer emulsion[*13] | 0.4 | 0.4 | 0.4 | 0.4 | 0.4 | 0.4 | 0.4 | 0.4 | 0.4 | 0.4 |
| 95% synthetic ethylalcohol | 15.0 | 15.0 | 15.0 | 15.0 | 15.0 | 15.0 | 15.0 | 15.0 | 15.0 | 15.0 |
| Neopentyl glycol dicaprate |  |  |  |  |  |  |  |  |  |  |
| Isopropyl palmitate |  |  |  |  |  |  |  |  |  |  |
| Polyethylene glycol | 0.2 |  | 0.2 |  | 0.2 |  | 0.2 |  | 0.2 |  |
| Glycerine |  | 1.0 |  | 1.0 |  | 1.0 |  | 1.0 |  | 1.0 |
| Purified water | Balance | Balance | Balance | Balance | Balance | Balance | Balance | Balance | Balance | Balance |
| Sodium hydroxide | As required | As required | As required | As required | As required | As required | As required | As required | As required | As required |
| Perfume | 0.1 | 0.1 | 0.1 | 0.1 | 0.1 | 0.1 | 0.1 | 0.1 | 0.1 | 0.1 |
| Propellant (LPG, 4.4 MPa) |  |  |  |  |  |  |  |  |  |  |
| pH | 3.7 | 3.7 | 3.7 | 3.7 | 3.7 | 3.7 | 3.7 | 3.7 | 3.7 | 3.7 |

TABLE 11

|  | Reference Examples |  |  |  |  |  |  |  |  |  |  |  |
|---|---|---|---|---|---|---|---|---|---|---|---|---|
|  | 31 | 32 | 33 | 34 | 35 | 36 | 37 | 38 | 39 | 40 | 41 | 42 |
| Aqueous malic acid (50% by mass aqueous solution) | 3.5 |  | 1.0 |  |  |  | 3.5 |  |  | 3.5 |  |  |
| Lactic acid (90% by mass aqueous solution) |  | 2.0 | 1.5 |  |  |  |  | 2.0 |  |  |  |  |
| Glycolic acid (70% by mass aqueous solution) |  |  |  |  |  |  |  |  | 2.5 |  |  |  |
| Citric acid (50% by mass aqueous solution) |  |  |  |  |  |  |  |  |  |  |  |  |
| Benzyl alcohol |  |  |  | 1.0 | 0.2 |  | 0.2 | 0.2 | 0.2 |  | 0.2 |  |
| Dipropylene glycol |  |  |  |  | 0.8 |  | 0.8 | 0.8 | 0.8 |  | 0.8 |  |
| 1,3-Butylene glycol |  |  |  |  |  | 0.2 |  |  |  |  |  |  |
| Phenoxyethanol |  |  |  |  |  | 0.1 |  |  |  |  |  |  |
| Benzyloxyethanol |  |  |  |  |  | 1.0 |  |  |  |  |  |  |

TABLE 11-continued

|  | Reference Examples | | | | | | | | | | | |
| --- | --- | --- | --- | --- | --- | --- | --- | --- | --- | --- | --- | --- |
|  | 31 | 32 | 33 | 34 | 35 | 36 | 37 | 38 | 39 | 40 | 41 | 42 |
| Organopolysiloxane A*[1] | 2.5 | 2.5 | 2.5 | 2.5 | 2.5 | 2.5 |  |  |  |  |  | 2.5 |
| Organopolysiloxane B*[2] | 0.1 | 0.1 | 0.1 | 0.1 | 0.1 | 0.1 |  |  |  |  |  | 0.1 |
| Organopolysiloxane D*[7] |  |  |  |  |  |  | 2.5 | 2.5 | 2.0 |  |  | 0.1 |
| Organopolysiloxane E*[8] |  |  |  |  |  |  |  |  |  | 1.0 |  | 0.1 |
| Vinylpyrrolidone-N,N-dimethylaminoethyl methacrylic acid copolymer diethyl sulfate | 0.5 | 0.5 | 0.5 | 0.5 | 0.5 | 0.5 | 0.5 | 0.5 | 0.5 | 0.5 | 0.5 | 1.5 |
| Stearyl trimethyl ammonium chloride (30% by mass aqueous solution) | 1.5 | 1.5 | 1.5 | 1.5 | 1.5 | 1.5 | 1.5 | 1.5 | 1.5 | 1.5 | 1.5 | 2.5 |
| Polyoxyethylene tridecyl ether*[9] | 0.5 | 0.5 | 0.5 | 0.5 | 0.5 | 0.5 | 0.5 | 0.5 | 0.5 | 0.5 | 0.5 | 1.5 |
| Polyoxyethylene-polyoxypropylene stearyl ether*[10] | 2.0 | 2.0 | 2.0 | 2.0 | 2.0 | 2.0 | 2.0 | 2.0 | 2.0 | 2.0 | 2.0 | 3.0 |
| Polyoxyethylene cetyl ether*[11] | 0.5 | 0.5 | 0.5 | 0.5 | 0.5 | 0.5 | 0.5 | 0.5 | 0.5 | 0.5 | 0.5 | 1.5 |
| Polyoxyethylene-methylpolysiloxane copolymer*[12] |  |  |  |  |  |  |  |  |  |  |  |  |
| 95% synthetic ethylalcohol | 12.0 | 12.0 | 12.0 | 12.0 | 12.0 | 12.0 | 12.0 | 12.0 | 12.0 | 12.0 | 12.0 | 13.0 |
| Neopentyl glycol dicaprate |  |  |  |  |  |  |  |  |  |  |  |  |
| Isopropyl palmitate |  |  |  |  |  |  |  |  |  |  |  |  |
| Purified water | Balance | Balance | Balance | Balance | Balance | Balance | Balance | Balance | Balance | Balance | Balance | Balance |
| Sodium hydroxide | As required | As required | As required | As required | As required | As required | As required | As required | As required | As required | As required | As required |
| Perfume | 0.1 | 0.1 | 0.1 | 0.1 | 0.1 | 0.1 | 0.1 | 0.1 | 0.1 | 0.1 | 0.1 | 1.1 |
| Propellant (LPG, 4.4 MPa) | 7.0 | 7.0 | 7.0 | 7.0 | 7.0 | 7.0 | 7.0 | 7.0 | 7.0 | 7.0 | 7.0 | 8.0 |
| pH | 3.7 | 3.7 | 3.7 | 6.0 | 6.0 | 6.0 | 3.7 | 3.7 | 3.7 | 3.7 | 6.0 | 6.0 |

TABLE 12

|  | Reference Examples | | | | | | | | | | | |
| --- | --- | --- | --- | --- | --- | --- | --- | --- | --- | --- | --- | --- |
|  | 43 | 44 | 45 | 46 | 47 | 48 | 49 | 50 | 51 | 52 | 53 | 54 |
| Aqueous malic acid (50% by mass aqueous solution) | 2.5 | 2.5 | 2.5 | 2.5 | 2.5 | 2.5 |  |  |  |  |  |  |
| Lactic acid (90% by mass aqueous solution) | 1.4 | 1.4 | 1.4 | 1.4 | 1.4 | 1.4 |  |  |  |  |  |  |
| Glycolic acid (70% by mass aqueous solution) |  |  |  |  |  |  |  |  |  |  |  |  |
| Citric acid (50% by mass aqueous solution) |  |  |  |  |  |  |  |  |  |  |  |  |
| Benzyl alcohol | 0.2 | 0.2 |  |  |  |  | 0.2 | 0.2 | 0.2 | 0.2 |  |  |
| Dipropylene glycol | 1.0 | 1.0 |  |  |  |  | 1.0 | 1.0 | 1.0 | 1.0 |  |  |
| 1,3-Butylene glycol |  |  |  |  |  |  |  |  |  |  |  |  |
| Phenoxyethanol |  |  |  |  |  |  |  |  |  |  |  |  |
| Benzyloxyethanol |  |  |  |  |  |  |  |  |  |  |  |  |
| Organopolysiloxane A*[1] |  |  | 0.4 | 1.9 |  |  | 0.4 | 1.9 |  |  | 0.4 | 1.9 |
| Organopolysiloxane B*[2] |  |  |  |  |  |  |  |  |  |  |  |  |
| Organopolysiloxane D*[7] |  |  | 1.5 | 1.3 |  |  | 1.5 | 1.3 |  |  | 1.5 | 1.3 |
| Organopolysiloxane E*[8] |  |  |  |  |  |  |  |  |  |  |  |  |
| Vinylpyrrolidone-N,N-dimethylaminoethyl methacrylic acid copolymer diethyl sulfate | 0.2 | 1.0 | 0.2 | 1.0 | 0.2 | 1.0 | 0.2 | 1.0 | 0.2 | 1.0 | 0.2 | 1.0 |
| Stearyl trimethyl ammonium chloride (30% by mass aqueous solution) | 0.8 | 0.8 | 0.8 | 0.8 | 0.8 | 0.8 | 0.8 | 0.8 | 0.8 | 0.8 | 0.8 | 0.8 |
| Polyoxyethylene tridecyl ether*[9] | 0.2 | 0.4 | 0.2 | 0.4 | 0.2 | 0.4 | 0.2 | 0.4 | 0.2 | 0.4 | 0.2 | 0.4 |
| Polyoxyethylene-polyoxypropylene stearyl ether*[10] |  |  |  |  |  |  |  |  |  |  |  |  |
| Polyoxyethylene cetyl ether*[11] |  |  |  |  |  |  |  |  |  |  |  |  |
| Polyoxyethylene-methyl polysiloxane copolymer*[12] |  | 0.6 |  | 0.6 |  | 0.6 |  | 0.6 |  | 0.6 |  | 0.6 |
| Aminoethylaminopropylsiloxane-dimethylsiloxane copolymer emulsion*[13] | 0.4 | 0.4 | 0.4 | 0.4 | 0.4 | 0.4 | 0.4 | 0.4 | 0.4 | 0.4 | 0.4 | 0.4 |
| 95% synthetic ethylalcohol | 15.0 | 15.0 | 15.0 | 15.0 | 15.0 | 15.0 | 15.0 | 15.0 | 15.0 | 15.0 | 15.0 | 15.0 |
| Neopentyl glycol dicaprate |  |  |  |  |  |  |  |  |  |  |  |  |

TABLE 12-continued

| | Reference Examples | | | | | | | | | | | |
|---|---|---|---|---|---|---|---|---|---|---|---|---|
| | 43 | 44 | 45 | 46 | 47 | 48 | 49 | 50 | 51 | 52 | 53 | 54 |
| Isopropyl palmitate | | | | | | | | | | | | |
| Polyethylene glycol | 0.2 | | 0.2 | | 0.2 | | 0.2 | | 0.2 | | 0.2 | |
| Glycerine | | 1.0 | | 1.0 | | 1.0 | | 1.0 | | 1.0 | | 1.0 |
| Purified water | Balance | Balance | Balance | Balance | Balance | Balance | Balance | Balance | Balance | Balance | Balance | Balance |
| Sodium hydroxide | As required | As required | As required | As required | As required | As required | As required | As required | As required | As required | As required | As required |
| Perfume | 0.1 | 0.1 | 0.1 | 0.1 | 0.1 | 0.1 | 0.1 | 0.1 | 0.1 | 0.1 | 0.1 | 0.1 |
| Propellant (LPG, 4.4 MPa) | | | | | | | | | | | | |
| pH | 3.7 | 3.7 | 3.7 | 3.7 | 3.7 | 3.7 | 3.7 | 3.7 | 3.7 | 3.7 | 3.7 | 3.7 |

*[1]Organopolysiloxane obtained in Example 10
*[2]Organopolysiloxane obtained in Example 11
*[7]Organopolysiloxane obtained in Comparative Example 10
*[8]Organopolysiloxane obtained in Comparative Example 9
*[9]SOFTANOL 90 (Nippon Shokubai Co., Ltd.)
*[10]UNILUBE YM-250 (NOF Corporation)
*[11]Nikkol BC-20TX (Nihon Surfactant Kogyo K.K.)
*[12]KF6029 (Shin-Etsu Chemical Co., Ltd.)
*[13]SM8704C (Dow Corning Toray Co., Ltd.)

The foam-type hair cosmetics obtained in these examples and reference examples were evaluated for "setting performance," "set holding performance," "softness of hair," "manageability," "no greasiness," "effects of improving firmness and body after shampooing," and "manageability after shampooing" according to the following method and criteria.

Evaluation Method

A panel of five female experts with hair longer than the shoulder (medium length, long) who had permanent wave within three months received a foam-type hair cosmetic obtained in each example or reference example on the head hair as required (3 to 5 g) and made evaluation as follows.

(1) Setting Performance

After styling, setting performance was evaluated with the completely dried hair.

(2) Set Holding Performance

After styling, the hair was dried completely and left for 4 hours, and then setting performance was evaluated.

(3) Softness of Hair

After styling, softness of hair was evaluated with the completely dried hair.

(4) Manageability

After styling, hair manageability was evaluated with the completely dried hair.

(5) No Greasiness

After styling, hair greasiness was evaluated with the completely dried hair.

(6) Effects Improving Firmness and Body after Shampooing

After evaluations of (1) to (5), the hair was washed with the model shampoo shown in Table 3, effects of improving firmness and body were evaluated with the air-dried hair.

(7) Manageability after Shampooing

After evaluations of (1) to (5), the hair was washed with the model shampooing shown in Table 3, manageability was evaluated with the air-dried hair.

Evaluation Criteria

Sensory evaluation was made by a panel of five experts according to the criteria shown in Table 13, evaluation points of each expert were added up, and evaluation was made according to the criteria shown below. The results of Examples 31 to 46 are shown in Table 14. The results of Examples 47 to 56 are shown in Table 15. The results of Reference Examples 31 to 42 are shown in Table 16. The results of Reference Examples 43 to 54 are shown in Table 17.

TABLE 13

(Setting performance)

5: Setting performance observed
4: Slight setting performance observed
3: Undecided
2: Minimal setting performance observed
1: No setting performance observed (Set holding performance)

5: Holding performance observed
4: Slight Holding performance observed
3: Undecided
2: Minimal holding performance observed
1: No holding performance observed (Softness of hair)

5: Soft
4: Slightly soft
3: Undecided
2: Not very soft
1: Not soft (No greasiness)

5: Not greasy
4: Not very greasy
3: Undecided
2: Slightly greasy
1: Greasy (Manageability)

5: Manageable
4: Slightly manageable
3: Undecided
2: Slightly poor manageability
1: Poor manageability (Effects improving firmness and body after shampooing)

5: Feel firmness and body effects
4: Feel slight firmness and body effects

TABLE 13-continued

3: Undecided
2: Feel not much firmness and body effects
1: Feel no firmness and body effects
(Manageability after shampooing)
5: Feel manageability
4: Feel slight manageability
3: Undecided
2: Feel minimal manageability
1: Feel no manageability Evaluation Criteria
A: The total score is 22 points or higher.
B: The total score is lower than 22 points and 17 points or higher.
C: The total score is lower than 17 points and 11 points or higher.
D: The total score is lower than 11 points.

TABLE 14

| | Examples | | | | | | | | | | | | | | | |
|---|---|---|---|---|---|---|---|---|---|---|---|---|---|---|---|---|
| | 31 | 32 | 33 | 34 | 35 | 36 | 37 | 38 | 39 | 40 | 41 | 42 | 43 | 44 | 45 | 46 |
| Setting performance | A | A | A | A | B | B | B | B | A | A | A | B | A | A | A | A |
| Set holding performance | A | A | B | B | A | B | A | B | A | A | A | A | A | B | A | A |
| Softness of hair | B | B | B | B | A | A | A | A | B | B | B | B | A | A | B | B |
| Manageability | B | B | B | B | B | A | B | A | B | B | B | A | A | B | B | A |
| No greasiness | A | A | A | A | A | C | B | C | B | B | B | B | B | A | A | C |
| Effects of improving firmness and body after shampooing | A | A | B | B | B | B | B | B | B | C | A | A | A | B | B | B |
| Manageability after shampooing | B | B | B | B | B | B | A | B | C | B | C | B | A | B | B | A |

TABLE 15

| | Examples | | | | | | | | | |
|---|---|---|---|---|---|---|---|---|---|---|
| | 47 | 48 | 49 | 50 | 51 | 52 | 53 | 54 | 55 | 56 |
| Setting performance | B | A | B | A | B | B | B | A | B | A |
| Set holding performance | A | A | A | A | B | B | B | A | A | A |
| Softness of hair | A | B | B | B | A | A | A | B | A | B |
| Manageability | B | A | B | B | A | A | A | A | B | A |
| No greasiness | A | B | B | C | B | B | C | C | A | B |
| Effects of improving firmness and body after shampooing | A | A | A | A | B | B | A | A | B | B |
| Manageability after shampooing | A | A | A | A | B | B | A | A | B | B |

TABLE 16

| | Reference Examples | | | | | | | | | | | |
|---|---|---|---|---|---|---|---|---|---|---|---|---|
| | 31 | 32 | 33 | 34 | 35 | 36 | 37 | 38 | 39 | 40 | 41 | 42 |
| Setting performance | B | B | B | B | B | B | C | C | C | D | D | A |
| Set holding performance | B | B | B | B | B | B | D | D | D | D | D | B |
| Softness of hair | C | C | C | C | C | C | B | B | A | D | D | B |
| Manageability | B | B | B | B | B | B | C | C | C | D | D | B |
| No greasiness | B | B | B | B | B | B | B | B | B | C | C | B |
| Effects of improving firmness and body after shampooing | D | D | D | D | D | D | B | B | B | D | D | D |
| Manageability after shampooing | D | D | D | C | C | C | B | B | B | D | C | D |

TABLE 17

|  | Reference Examples | | | | | | | | | | | |
|---|---|---|---|---|---|---|---|---|---|---|---|---|
|  | 43 | 44 | 45 | 46 | 47 | 48 | 49 | 50 | 51 | 52 | 53 | 54 |
| Setting performance | D | D | C | B | D | D | C | C | D | D | D | B |
| Set holding performance | D | D | C | C | D | D | D | C | D | D | D | C |
| Softness of hair | D | C | B | C | D | D | B | C | D | D | C | C |
| Manageability | D | D | B | B | D | D | C | B | D | D | C | C |
| No greasiness | D | C | B | C | C | C | C | D | C | C | C | C |
| Effects of improving firmness and body after shampooing | B | B | D | D | D | D | C | C | D | D | D | D |
| Manageability after shampooing | B | B | D | D | D | D | C | C | D | D | D | D |

Preparation examples of hair cosmetics containing the organopolysiloxane of the present invention will be shown below.

Preparation Example 1

Pump Spray

|  | (% by mass) |
|---|---|
| Organopolysiloxane A (Example 10) | 0.5 |
| Stearyltrimethyl ammonium chloride | 0.25 |
| Glycerine | 1.0 |
| Ethanol | 4.5 |
| Perfume | 0.02 |
| Water | Balance |

Preparation Example 2

Pump Mist

|  | (% by mass) |
|---|---|
| Organopolysiloxane A (Example 10) | 0.2 |
| Organopolysiloxane B (Example 11) | 0.2 |
| Polyvinylpyrrolidone | 3.0 |
| Ethanol | 10.0 |
| Perfume | 0.05 |
| Water | Balance |

Preparation Example 3

Hair Gel

|  | (% by mass) |
|---|---|
| Organopolysiloxane A (Example 10) | 1.2 |
| Organopolysiloxane F (Example 6) | 1.5 |
| Glycerine | 2.0 |
| Hydroxyethylcellulose | 2.0 |
| Ethanol | 10.0 |
| Perfume | 0.05 |
| Water | Balance |

Preparation Example 4

Hair Lotion

|  | (% by mass) |
|---|---|
| Organopolysiloxane A (Example 10) | 0.2 |
| Organopolysiloxane G (Example 4) | 0.2 |
| Glycerine | 1.0 |
| Ethanol | 10.0 |
| Perfume | 0.02 |
| Water | Balance |

Preparation Example 5

Hair Lotion

|  | (% by mass) |
|---|---|
| Organopolysiloxane B (Example 11) | 0.2 |
| Stearyltrimethyl ammonium chloride | 0.1 |
| Polyethylene glycol 400 | 0.45 |
| Ethanol | 4.5 |
| Water | Balance |

Preparation Example 6

Pump Foam

|  | (% by mass) |
|---|---|
| Organopolysiloxane A (Example 10) | 1.0 |
| Polyoxyethylene lauryl ether (16 E.O.) | 1.0 |
| Stearyltrimethyl ammonium chloride | 0.1 |
| Glycerine | 1.0 |
| Ethanol | 4.0 |
| Perfume | 0.02 |
| Water | Balance |

Preparation Example 7

Styling Pump Mist

|  | (% by mass) |
| --- | --- |
| Malic acid | 2.0 |
| Benzyl alcohol | 0.5 |
| Organopolysiloxane A (Example 10) | 1.1 |
| Stearyltrimethyl ammonium chloride | 0.3 |
| Glycerine | 2.0 |
| Ethanol | 9.5 |
| Perfume | 0.01 |
| Water | Balance |
| Sodium hydroxide (pH modifier) | Adjusted to pH 3.7 |

Preparation Example 8

Styling Pump Mist

|  | (% by mass) |
| --- | --- |
| Malic acid | 1.5 |
| Lactic acid | 2.0 |
| 2-Benzyloxyethanol | 1.0 |
| Dipropylene glycol | 0.5 |
| Polyoctanium-11*[14] | 0.7 |
| Organopolysiloxane A (Example 10) | 2.8 |
| Organopolysiloxane B (Example 11) | 0.2 |
| Ethanol | 12.0 |
| Perfume | 0.01 |
| Water | Balance |
| Sodium hydroxide (pH modifier) | Adjusted to pH 3.7 |

*[14]GAFQUATS 755N, ISP Japan Ltd.

Preparation Example 9

Styling Gel

|  | (% by mass) |
| --- | --- |
| Malic acid | 1.5 |
| Citric acid | 1.5 |
| Glycerine | 2.0 |
| Benzyl alcohol | 0.3 |
| 1,3-Butylene glycol | 1.0 |
| Organopolysiloxane A (Example 10) | 1.5 |
| Organopolysiloxane B (Example 11) | 0.5 |
| Hydroxyethylcellulose*[15] | 2.0 |
| Ethanol | 25.0 |
| perfume | 0.02 |
| Water | Balance |
| Sodium hydroxide (pH modifier) | Adjusted to pH 3.7 |

*[15]HEC Daicel SE850K, Daicel Chemical Industries, Ltd.

Preparation Example 10

Styling Lotion

|  | (% by mass) |
| --- | --- |
| Malic acid | 1.2 |
| Lactic acid | 1.0 |
| Benzyl alcohol | 0.3 |
| Dipropylene glycol | 0.5 |
| Organopolysiloxane A (Example 10) | 1.6 |
| Organopolysiloxane D (Comparative Example 10) | 0.5 |
| Glycerine | 1.0 |
| Ethanol | 12.0 |
| Perfume | 0.02 |
| Water | Balance |
| Sodium hydroxide (pH modifier) | Adjusted to pH 3.7 |

Preparation Example 11

Styling Lotion

|  | (% by mass) |
| --- | --- |
| Malic acid | 1.5 |
| Glycolic acid | 1.0 |
| Benzyl alcohol | 0.5 |
| Phenoxyethanol | 0.3 |
| Organopolysiloxane B (Example 11) | 0.8 |
| Organopolysiloxane C (Example 6) | 0.5 |
| Polyethylene glycol (MW = 400)*[16] | 0.45 |
| Stearyltrimethyl ammonium chloride | 0.1 |
| Ethanol | 7.5 |
| Water | Balance |
| Sodium hydroxide (pH modifier) | Adjusted to pH 3.7 |

*[16]ADEKA PEG400, ADEKA Corporation

Preparation Example 12

Styling Pump Foam

|  | (% by mass) |
| --- | --- |
| Malic acid | 1.0 |
| Lactic acid | 1.5 |
| Glycerine | 1.0 |
| Benzyl alcohol | 0.2 |
| Dipropylene glycol | 0.7 |
| 1,3-Butylene glycol | 0.3 |
| Organopolysiloxane A (Example 10) | 1.2 |
| Organopolysiloxane B (Example 11) | 0.7 |
| Organopolysiloxane D (Comparative Example 10) | 0.5 |
| Polyoctanium-11*[14] | 0.5 |
| Polyoxyethylene tridecyl ether | 1.0 |
| Stearyltrimethyl ammonium chloride | 0.2 |
| Ethanol | 5.5 |
| Perfume | 0.01 |
| Water | Balance |
| Sodium hydroxide (pH modifier) | Adjusted to pH 3.7 |

*[14]GAFQUATS 755N, ISP Japan Ltd.

Preparation Example 13

Hair Cream, pH 3.7

|  | (% by mass) |
|---|---|
| Organopolysiloxane A (Example 10) | 0.7 |
| Organopolysiloxane B (Example 11) | 0.3 |
| Organopolysiloxane D (Comparative Example 10) | 0.3 |
| Behenyltrimethyl ammonium chloride | 0.24 |
| Malic acid | 0.5 |
| Benzyl alcohol | 0.2 |
| Dipropylene glycol | 2.0 |
| N,N-Dimethyloctadecyloxypropylamine | 0.2 |
| Cetanol | 1.6 |
| Isopropyl palmitate | 0.5 |
| Dimethicone (Dow Corning Toray Co., Ltd., BY22-060) | 0.5 |
| Perfume | 0.1 |
| pH modifier (sodium hydroxide, lactic acid) | As required |
| Water | Balance |

The invention claimed is:

1. A method of setting hair, comprising:
(1) applying a hair cosmetic to hair;
(2) setting said hair in a desired shape, before drying after said (1) applying; and
(3) removing an organic solvent from said hair cosmetic;
wherein the hair cosmetic comprises:
an organic solvent; and
an organopolysiloxane comprising:
(i) an organopolysiloxane segment as a main chain, and
(ii) two or more poly(N-acylalkyleneimine) segments each containing a repeating unit represented by formula (1):

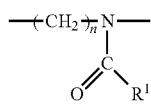

(1)

wherein $R^1$ represents a hydrogen atom, an alkyl group having 1 to 22 carbon atoms, an aralkyl group having 7 to 15 carbon atoms, or an aryl group having 6 to 14 carbon atoms, and n is 2 or 3,
wherein each poly(N-acylalkyleneimine) segment is bound to a silicon atom of said organopolysiloxane segment via an alkylene group comprising a hetero atom,
wherein a number-average molecular weight of each poly(N-acylalkyleneimine) segment is 800 g/mol to 1600 g/mol as measured by gel permeation chromatography,
wherein a weight-average molecular weight of said organopolysiloxane segment is 10,000 g/mol to 100,000 g/mol as measured by gel permeation chromatography,
wherein a mass ratio (a/b) of said organopolysiloxane segment (a) to said two or more poly(N-acylalkyleneimine) segments (b) is 65/35 to 82/18, as calculated from an NMR measurement, and
wherein a weight-average molecular weight (MWg) of a portion of said organopolysiloxane segment between adjacent poly(N-acylalkyleneimine) segments is 1700 g/mol to 3000 g/mol, wherein MWg is given by formula (I):

$$MWg = \frac{Csi \times MWox}{100 - Csi}, \quad (I)$$

wherein Csi is a content percentage of the organopolysiloxane segment as a main chain, and MWox is a number-average molecular weight, as measured by gel permeation chromatography, of a poly(N-acylalkyleneimine) segment adjacent to said portion of said organopolysiloxane segment.

2. The method according to claim 1, wherein the organic solvent comprises one or more organic solvents selected from the group consisting of (b1), (b2), (b3), (b4), and (b5):
(b1) a compound represented by formula (2)

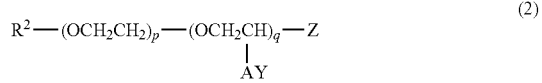

(2)

wherein $R^2$ represents a hydrogen atom, an alkyl group having 1 to 6 carbon atoms, or a group $R^3$-Ph-$R^4$-, wherein $R^3$ represents a hydrogen atom, a methyl group, or a methoxy group; $R^4$ represents a bond or a saturated or unsaturated divalent hydrocarbon group having 1 to 3 carbon atoms; and Ph represents a paraphenylene group, A represents a bond or a saturated divalent hydrocarbon group having 1 to 4 carbon atoms, Y and Z each independently represent a hydrogen atom or a hydroxy group, and p and q each independently are an integer of 0 to 5, provided that when p=q=0, Z represents a hydroxy group, and $R^2$ is not either a hydrogen atom or a group $R^3$-Ph-;
(b2) N-alkylpyrrolidone or N-alkenylpyrrolidone in which an alkyl group or an alkenyl group having 1 to 18 carbon atoms is bonded to a nitrogen atom;
(b3) an alkylene carbonate having 2 to 4 carbon atoms;
(b4) a polypropylene glycol having a number-average molecular weight of 100 g/mol to 1000 g/mol as measured by gel permeation chromatography; and
(b5) a lactone or a cyclic ketone represented by formula (3), (4), or (5):

(3)

(4)

(5)

wherein X represents a methylene group or an oxygen atom, $R^5$ and $R^6$ represent substituents different from each other, and a and b each independently are 0 or 1.

3. The method according to claim 2, wherein said organic solvent comprises at least one of dipropylene glycol, 1,3-butanediol, benzyl alcohol, phenoxyethanol, 2-benzyloxyethanol, propylene carbonate, and polypropylene glycol having a number-average molecular weight of 300 g/mol to 500 g/mol as measured by gel permeation chromatography.

4. The method according to claim 2, wherein said organic solvent is a lower alcohol having 1 to 6 carbon atoms.

5. The method according to claim 4, wherein said hair cosmetic further comprises an organic carboxylic acid which may contain a hydroxy group or a salt thereof.

6. The method according to claim 5, wherein said organic carboxylic acid which may contain a hydroxy group is a hydroxycarboxylic acid having 2 to 6 carbon atoms.

7. The method according to claim 1, wherein the hair cosmetic further comprises a set polymer.

8. The method according to claim 5, wherein the hair cosmetic has a pH of 2.5 to 4.5 at 25° C. when diluted 20-fold by mass with water.

9. The method according to claim 1, wherein the hair cosmetic is a semisolid styling composition.

10. The method according to claim 1, wherein, in the hair cosmetic, said two or more poly(N-acylalkyleneimine) segments are bound to silicon atoms that are not terminal silicon atoms of said organopolysiloxane segment via the alkylene group comprising a hetero atom.

11. The method according to claim 1, wherein, in the hair cosmetic, the mass ratio (a/b) is 70/30 to 79/21.

12. The method according to claim 1, wherein the content of the organosiloxane is 0.05 to 20% by mass of the hair cosmetic.

13. The method according to claim 1, wherein the total content of said organic solvent is 0.1 to 40% by mass of the hair cosmetic.

14. The method according to claim 5, wherein the total content of said organic carboxylic acid is 0.1 to 30% by mass of the hair cosmetic.

15. The method according to claim 5, wherein a mass ratio of said organic carboxylic acid to said organic solvent is 10:1 to 1:7.

16. The method according to claim 7, wherein, said set polymer is at least one member selected from the group consisting of a vinylpyrrolidone polymer, an acidic vinyl ether polymer, an acidic polyvinyl acetate polymer, an acidic acrylic polymer, an ampholytic acrylic polymer, a (meth) acryl ethyl betaine/alkyl (meth)acrylate copolymer, a basic acrylic polymer, a cellulose derivative, a chitin derivative, and a chitosan derivative.

17. The method according to claim 7, wherein the content of said set polymer is 0.05 to 20% by mass of the total mass of a hair cosmetic.

18. The method according to claim 1, wherein the hair cosmetic further comprises an oil solution.

19. The method according to claim 1, wherein said (2) setting is carried out with a brush, a dryer, a flat iron, or a curler.

20. The method according to claim 1, wherein said (3) removing occurs by natural drying or heating.

* * * * *

UNITED STATES PATENT AND TRADEMARK OFFICE
CERTIFICATE OF CORRECTION

PATENT NO.         : 10,456,351 B2
APPLICATION NO.    : 15/000284
DATED              : October 29, 2019
INVENTOR(S)        : Kazuhisa Fukuhara et al.

Page 1 of 1

It is certified that error appears in the above-identified patent and that said Letters Patent is hereby corrected as shown below:

In the Claims

Column 50, Line 20-21:
Please replace "of said set polymer is 0.05 to 20% by mass of the total mass of a hair cosmetic." with --of said set polymer is 0.05 to 20% by mass of the total mass of the hair cosmetic.--

Signed and Sealed this
Eleventh Day of February, 2020

Andrei Iancu
*Director of the United States Patent and Trademark Office*

UNITED STATES PATENT AND TRADEMARK OFFICE
CERTIFICATE OF CORRECTION

PATENT NO. : 10,456,351 B2
APPLICATION NO. : 15/000284
DATED : October 29, 2019
INVENTOR(S) : Kazuhisa Fukuhara et al.

It is certified that error appears in the above-identified patent and that said Letters Patent is hereby corrected as shown below:

In the Claims

Column 50, Line 20-21 Claim 17:
Please replace "of said set polymer is 0.05 to 20% by mass of the total mass of a hair cosmetic." with --of said set polymer is 0.05 to 20% by mass of the hair cosmetic.--

This certificate supersedes the Certificate of Correction issued February 11, 2020.

Signed and Sealed this
Seventeenth Day of March, 2020

Andrei Iancu
*Director of the United States Patent and Trademark Office*